US010799517B2

(12) United States Patent
Baheti et al.

(10) Patent No.: US 10,799,517 B2
(45) Date of Patent: *Oct. 13, 2020

(54) ORAL COMPOSITION OF CELECOXIB FOR TREATMENT OF PAIN

(71) Applicant: Dr. Reddy's Laboratories Ltd., Hyderabad, Telangana (IN)

(72) Inventors: Ankit Baheti, Indore (IN); Bijay Kumar Padhi, Buguda (IN); Supritha Vakada, Hyderabad (IN); Rajeev Singh Raghuvanshi, Gurgaon (IN)

(73) Assignee: DR. REDDY'S LABORATORIES LTD, Hyderabad, Telangana (IN)

(*) Notice: Subject to any disclaimer, the term of this patent is extended or adjusted under 35 U.S.C. 154(b) by 0 days.

This patent is subject to a terminal disclaimer.

(21) Appl. No.: 15/922,353

(22) Filed: Mar. 15, 2018

(65) Prior Publication Data

US 2018/0200271 A1  Jul. 19, 2018

Related U.S. Application Data

(63) Continuation of application No. 15/712,415, filed on Sep. 22, 2017, now Pat. No. 9,949,990, which is a continuation of application No. 15/374,951, filed on Dec. 9, 2016, now Pat. No. 9,795,620, which is a continuation of application No. 15/167,922, filed on May 27, 2016, now Pat. No. 9,572,819.

(30) Foreign Application Priority Data

May 28, 2015 (IN) .......................... 2682/CHE/2015
Dec. 10, 2015 (IN) .......................... 6614/CHE/2015

(51) Int. Cl.
*A61K 31/415* (2006.01)
*A61K 31/635* (2006.01)
*A61K 47/14* (2017.01)
*A61K 47/44* (2017.01)
*A61K 9/00* (2006.01)
*A61K 9/08* (2006.01)
*A61K 47/10* (2017.01)
*A61K 9/10* (2006.01)
*A61K 47/26* (2006.01)
*C07D 231/12* (2006.01)

(52) U.S. Cl.
CPC .......... *A61K 31/635* (2013.01); *A61K 9/0053* (2013.01); *A61K 9/0095* (2013.01); *A61K 9/08* (2013.01); *A61K 9/10* (2013.01); *A61K 31/415* (2013.01); *A61K 47/10* (2013.01); *A61K 47/14* (2013.01); *A61K 47/26* (2013.01); *A61K 47/44* (2013.01); *C07D 231/12* (2013.01)

(58) Field of Classification Search
CPC .................................................. A61K 31/415
USPC ...................................................... 514/406
See application file for complete search history.

(56) References Cited

U.S. PATENT DOCUMENTS 9,572,819 B2 * 2/2017 Baheti ..................... A61K 47/26
9,795,620 B2 * 10/2017 Baheti ..................... A61K 47/26
9,949,990 B2 * 4/2018 Baheti ..................... A61K 47/26

FOREIGN PATENT DOCUMENTS

| JP | 2003-503440 A | 1/2003 |
| JP | 2004-500427 A | 1/2004 |
| JP | 2007-512373 A | 5/2007 |
| KR | 1020130115650 A | 10/2013 |
| KR | 10-2013-0115650 | 6/2014 |
| KR | 1020140100170 A | 8/2014 |
| MX | 349193 B | 2/2015 |
| WO | 2001/001960 A1 | 1/2001 |
| WO | 01/78724 A1 | 10/2001 |
| WO | 01/91750 A1 | 12/2001 |
| WO | 2004/047752 A2 | 6/2004 |
| WO | 2005/053612 A2 | 6/2005 |
| WO | 2010/150144 A2 | 12/2010 |

OTHER PUBLICATIONS

Instituto Mexicano De La Propiedad Industrial (Mexican Patent Office), Office Action issued in corresponding Application No. MX/a/2017/015238 dated Oct. 2, 2018. (Translation not available.).
Subramanian et al., "Formulation Design of Self-Microemulsifying Drug Delivery Systems for Improved Oral Bioavailability of Celecoxib", Biological and Pharmaceutical Bulletin, (2004), vol. 27, No. 12, pp. 1993-1999.
Zvonar et al, "The Influence of Microstructure on Celecoxib Release from a Pharmaceutically Applicable System: Mygliol 812®/Labrasol®/ Plurol Oleique®/Water Mixtures", Acta Chim Slov, (2009), vol. 56, pp. 131-138.
Claire E O'Hanlon et al, "NIR-labeled perfluoropolyether nanoemulsions for drug delivery and imaging", Journal of Fluorine Chemistry, Elsevier, NL, vol. 137 (2012), pp. 27-33.
Natesan Subramanian, et al. "Topical delivery of celecoxib using microemulsion", Biopharmacy, Acta Poloniae Pharmaceutica— Drug Research, vol. 61, No. 5, 2004, pp. 335-341.
Japan Patent Office, Office Action (Notice of Reasons for Refusal) issued in corresponding Application No. 2017-561947 dated Sep. 5, 2018. (Partial translation).
Canadian Intellectual Property Office, Examiner's Report issued in corresponding Application No. 2,987,272 dated Jun. 14, 2018.
Canadian Intellectual Property Office, Examiner's Report issued in corresponding Application No. 2,987,272, dated Mar. 7, 2019.

(Continued)

*Primary Examiner* — Raymond J Henley, III
(74) *Attorney, Agent, or Firm* — Stites & Harbison, PLLC; Mandy Wilson Decker

(57) ABSTRACT

The present invention relates to a stable oral liquid pharmaceutical composition of celecoxib or its pharmaceutically acceptable salts thereof. The celecoxib present in the compositions as described herein do not show any precipitation when subjected in Fasted-State Simulated Gastric Fluid (FaSSGF) at pH 2.0, temperature of 37° C.±0.5° C. and under stirring at a speed of 50 rpm at least for 60 minutes. It also relates to the process of preparing and method of using said composition of celecoxib.

26 Claims, 5 Drawing Sheets

(56) References Cited

OTHER PUBLICATIONS

Japan Patent Office, Office Action (Notice of Reasons for Refusal) issued in corresponding Application No. JP 2017-561947, dated Apr. 16, 2019. (Partial translation.).
Eurasian Patent Organization, Office Action entered in corresponding Application No. 201792530, dated May 1, 2019. (An English translation is not available.).

* cited by examiner

ORAL COMPOSITION OF CELECOXIB FOR TREATMENT OF PAIN

PRIORITY

This application claims priority to U.S. patent application Ser. No. 15/712,415, filed Sep. 22, 2017, now issued as U.S. Pat. No. 9,949,990, which claims priority to U.S. Pat. No. 9,795,620 issued from U.S. patent application Ser. No. 15/374,951, filed Dec. 9, 2016, which claims priority to U.S. Pat. No. 9,572,819 issued from U.S. patent application Ser. No. 15/167,922, filed May 27, 2016, which claims priority to Indian Patent Application Nos. 2682/CHE/2015, filed May 28, 2015, and 6614/CHE/2015, filed Dec. 10, 2015, the entire disclosures of which are incorporated herein by reference in their entireties.

BACKGROUND

Non-steroidal anti-inflammatory drugs (NSAID) are generally used for the treatment of acute pain, inflammatory pain, visceral pain, breakthrough pain, nociceptive pain, neuropathic pain, dysmenorrhea, post-surgical pain, acute postpartum pain, postoperative pain management chronic pain in osteoarthritis, rheumatoid arthritis and pain due to other diseases and causes.

Celecoxib is approved in U.S. under brand name CELEBREX®, as oral capsules and used in the treatment of osteoarthritis, rheumatoid arthritis, juvenile rheumatoid arthritis, ankylosing spondylitis, acute pain, chronic pain, primary dysmenorrhea and familial adenomatous polyposis. It is available in the strengths of 50 mg, 100 mg, 200 mg and 400 mg.

Celecoxib was described in U.S. Pat. No. 5,466,823 assigned to Searle, a class of 1,5-diaryl pyrazoles and their salts together with processes for the preparation of such compounds.

Celecoxib is chemically designated as 4-[5-(4-methylphenyl)-3-(trifluoromethyl)-1H-pyrazol-1-yl] benzenesulfonamide and is a diaryl-substituted pyrazole. The empirical formula is $C_{17}H_{14}F_3N_3O_2S$, and the molecular weight is 381.38; the chemical structure is as follows:

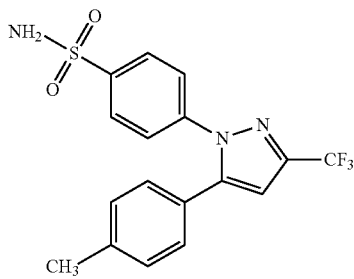 [SMILES: Cc1ccc(-c2cc(C(F)(F)F)nn2-c2ccc(S(N)(=O)=O)cc2)cc1]

U.S. Pat. No. 5,466,823 contains general references to formulations for the administration of 1,5-diaryl pyrazoles, including orally deliverable dosage forms such as tablets and capsules.

U.S. Pat. No. 5,760,068 describes a class of 1,5-diaryl pyrazole compounds including celecoxib that are selective inhibitors of cyclooxygenase-2 and can be administered to treat, among other conditions and disorders, pathological conditions associated with rheumatoid arthritis and osteoarthritis.

Celecoxib is a hydrophobic and highly permeable drug belonging to class II of biopharmaceutics classification system. Celecoxib is a neutral molecule that is essentially insoluble in water which leads to high variability in absorption and hence has limited bioavailability after oral administration. It also has pre-systemic metabolism.

Celecoxib has an aqueous solubility of about 5 µg/ml at between 5° C. and 40° C., which is pH independent at pH<9. Celecoxib is not readily dissolved and dispersed for rapid absorption in the gastrointestinal tract when administered orally, for example in capsule form. Oral administration is associated with a delayed onset of the desired pharmacological action. It is known that upon oral administration, celecoxib takes approximately 3.0 hours for peak plasma concentrations to be achieved and hence have delayed onset of action after administration. Additionally, the intake of food further influences drug absorption. However, acute pains, as in the case of migraine pain, surgical pain, trauma, pain due to kidney stones, and arthritis, demand immediate/faster pain relief.

Accordingly, there is a long felt need to develop a composition for celecoxib or its pharmaceutical salts thereof, which can be readily dissolved/dispersed for rapid absorption in the gastrointestinal tract in order to provide faster pain relief

SUMMARY

Some embodiments disclosed herein provide stable oral liquid pharmaceutical compositions, comprising a therapeutically effective amount of celecoxib, at least one solubiliser, at least one medium chain glyceride, at least one polar solvent, and at least one pharmaceutically acceptable excipient, wherein said composition does not show any precipitation in Fasted-State Simulated Gastric Fluid (FaSSGF) at pH of 2.0, temperature of 37° C.±0.5° C. and under stirring at a speed of 50 rpm, when measured at 60 min. In some embodiments, the composition is essentially free of precipitation inhibitors selected from the group consisting of polyvinyl caprolactam-polyvinyl acetate-polyethylene glycol graft copolymer (SOLUPLUS®), polyoxyethylene-polyoxypropylene block copolymers, pluronics, polyvinylpyrrolidone, and cellulosic polymers, including hydroxypropyl cellulose and hydroxypropyl methylcellulose. In some embodiments, the at least one solubiliser is polyethoxylated castor oil (available as KOLLIPHOR EL®), lauryl macrogolglyceride (available as GELUCIRE® 44/14), or a combination thereof. In some embodiments, the at least one medium chain glyceride is glyceryl tricaprylate/tricaprate (available as CAPTEX® 300), glyceryl monocaprylate (available as CAPMUL® MCM C8), or a combination thereof. In some embodiments, the at least one polar solvent is selected from the group consisting of propylene glycol, polyethylene glycols having a molecular weight between 400 and 1000, glycerin, C2 to C8 mono- and poly-alcohols (e.g., ethanol), C7 to C18 alcohols of linear or branched configuration, water and mixtures thereof. In some embodiments, the therapeutically effective amount of celecoxib comprises from about 1% to about 80% celecoxib by weight, based on the total weight of the composition. In some embodiments, the at least one solubiliser is present in an amount of from about 10% to about 70% by weight, based on the total weight of the composition. In some embodiments, a weight ratio of the at least one solubiliser to celecoxib varies from about 4.0:1.0 to about 20:1.0. In some embodiments, the at least one polar solvent is present in an amount of from about 20% to about 80% by weight, based on the total weight of the composition. In some embodiments, a weight ratio of the at least one solubiliser to the at least one polar solvent varies from about 0.60:1.00 to about 1.8:1.00. In some embodiments, the at least one medium chain glyceride is present in an amount of from about 5% to about 75% by weight, based on the total weight of the composition. In some embodiments, the composition has a mean oil droplet size of not more than 500 nm, when tested in 250 ml of Fasted-State Simulated Gastric Fluid (FaSSGF) at pH of 2.0, temperature of 37° C.±0.5° C. and under stirring at a speed of 50 rpm. In some embodiments, the composition has a viscosity of from about 20 cps to about 1000 cps. In some embodiments, the composition has a density of from about 0.8 gm/cm$^3$ to about 2 gm/cm$^3$. In some embodiments, the composition has a transmittance of at least 40%. In some embodiments, the composition has a pH of from about 3 to about 7. In some embodiments, the therapeutically effect amount of celecoxib is at least about 40% less than conventional celecoxib compositions such as CELEBREX® 400 mg oral capsules. In some embodiments, the therapeutically effect amount of celecoxib is about 240 mg. In some embodiments, the therapeutically effect amount of celecoxib is at least about 55% less than conventional celecoxib compositions such as CELEBREX® 400 mg oral capsules. In some embodiments, the therapeutically effect amount of celecoxib is about 180 mg. In some embodiments, the therapeutically effect amount of celecoxib is at least about 70% less than conventional celecoxib compositions such as CELEBREX® 400 mg oral capsules. In some embodiments, the therapeutically effect amount of celecoxib is about 120 mg. In some embodiments, the stable oral liquid pharmaceutical compositions, which upon oral administration to a human subject under fasting conditions, provides at least one of the following pharmacokinetic parameters:

$AUC_{(0-15\ min)}$ from about 10 ng·h/mL to about 80 ng·h/mL;

$AUC_{(0-30\ min)}$ from about 80 ng·h/mL to about 400 ng·h/mL;

$AUC_{(0-1\ hr)}$ from about 400 ng·h/mL to about 1500 ng·h/mL;

$AUC_{(0-2\ hr)}$ from about 1000 ng·h/mL to about 4000 ng·h/mL;

$AUC_{(0-t)}$ of at least about 2000 ng·h/mL;

$AUC_{(0-\infty)}$ of at least about 2000 ng·h/mL; and $T_{lag}$ of not more than 8 minutes.

In some embodiments, the stable oral liquid pharmaceutical compositions comprise: a) a therapeutically effective amount of celecoxib; b) at least one pharmaceutically acceptable excipient; c) at least one solubiliser in an amount from about 35% w/w to about 45% w/w; and d) at least one polar solvent in an amount from about 25% w/w to about 42% w/w, wherein the solubiliser and polar solvent are present in a ratio of from about 0.60:1 to about 1.8:1; and wherein the stable oral liquid pharmaceutical composition has a viscosity of from about 20 cps to about 1000 cps, and a density of from about 0.8 gm/cm$^3$ to about 2 gm/cm$^3$.

Some embodiments disclosed here provide stable oral liquid pharmaceutical compositions comprising from about 100 mg to 250 mg of celecoxib, at least one pharmaceutically acceptable excipient, at least one solubiliser, at least one medium chain glyceride, and at least one polar solvent, wherein the composition: a) releases no less than about 70% of the celecoxib at a period of 10 minutes; or b) releases no less than about 80% of the celecoxib at a period of 15 minutes, in 900 ml of 0.01N HCl with 0.5% sodium lauryl sulfate, when tested in a USP Type 2 apparatus with sinkers at 50 rpm and 37° C. In some embodiments, the composition is essentially free of precipitation inhibitors selected from the group consisting of polyvinyl caprolactam-polyvinyl acetate-polyethylene glycol graft copolymer (SOLUPLUS®), polyoxyethylene-polyoxypropylene block copolymers, pluronics, polyvinylpyrrolidone, and cellulosic polymers, including hydroxypropyl cellulose and hydroxypropyl methylcellulose. In some embodiments, the at least one solubiliser is polyethoxylated castor oil (available as KOLLIPHOR EL®), lauryl macrogolglyceride (available as GELUCIRE® 44/14), or a combination thereof. In some embodiments, the at least one medium chain glyceride is glyceryl tricaprylate/tricaprate (available as CAPTEX® 300), glyceryl monocaprylate (available as CAPMUL® MCM C8), or a combination thereof. In some embodiments, the at least one polar solvent is selected from the group consisting of propylene glycol, polyethylene glycols having a molecular weight between 400 and 1000, glycerin, C2 to C8 mono- and poly-alcohols (e.g., ethanol), C7 to C18 alcohols of linear or branched configuration, water and mixtures thereof. In some embodiments, the therapeutically effective amount of celecoxib comprises from about 1% to about 80% celecoxib by weight, based on the total weight of the composition. In some embodiments, the at least one solubiliser is present in an amount of from about 10% to about 70% by weight, based on the total weight of the composition. In some embodiments, a weight ratio of the at least one solubiliser to celecoxib varies from about 4.0:1.0 to about 20:1.0. In some embodiments, the at least one polar solvent is present in an amount of from about 20% to about 80% by weight, based on the total weight of the composition. In some embodiments, a weight ratio of the at least one solubiliser to the at least one polar solvent varies from about 0.60:1.00 to about 1.8:1.00. In some embodiments, the at least one medium chain glyceride is present in an amount of from about 5% to about 75% by weight, based on the total weight of the composition. In some embodiments, the composition has a mean oil droplet size of not more than 500 nm, when tested in 250 ml of Fasted-State Simulated Gastric Fluid (FaSSGF) at pH of 2.0, temperature of 37° C.±0.5° C. and under stirring at a speed of 50 rpm. In some embodiments, the composition has a viscosity of from about 20 cps to about 1000 cps. In some embodiments, the composition has a density of from about 0.8 gm/cm$^3$ to about 2 gm/cm$^3$. In some embodiments, the composition has a transmittance of at least 40%. In some embodiments, the composition has a pH of from about 3 to about 7. In some embodiments, the therapeutically effect amount of celecoxib is at least about 40% less than conventional celecoxib compositions such as CELEBREX® 400 mg oral capsules. In some embodiments, the therapeutically effect amount of celecoxib is about 240 mg. In some embodiments, the therapeutically effect amount of celecoxib is at least about 55% less than conventional celecoxib compositions such as CELEBREX® 400 mg oral capsules. In some embodiments, the therapeutically effect amount of celecoxib is about 180 mg. In some embodiments, the therapeutically effect amount of celecoxib is at least about 70% less than conventional celecoxib compositions such as CELEBREX® 400 mg oral capsules. In some embodiments, the therapeutically effect amount of celecoxib is about 120 mg. In some embodiments, the stable oral liquid pharmaceutical compositions, which upon oral administration to a human subject under fasting conditions, provides at least one of the following pharmacokinetic parameters:

$AUC_{(0-15\ min)}$ from about 10 ng·h/mL to about 80 ng·h/mL;

$AUC_{(0-30\ min)}$ from about 80 ng·h/mL to about 400 ng·h/mL;

$AUC_{(0\text{-}1\ hr)}$ from about 400 ng·h/mL to about 1500 ng·h/mL;

$AUC_{(0\text{-}2\ hr)}$ from about 1000 ng·h/mL to about 4000 ng·h/mL;

$AUC_{(0\text{-}t)}$ of at least about 2000 ng·h/mL;

$AUC_{(0\text{-}\infty)}$ of at least about 2000 ng·h/mL; and $T_{lag}$ of not more than 8 minutes.

In some embodiments, the stable oral liquid pharmaceutical compositions comprise: a) a therapeutically effective amount of celecoxib; b) at least one pharmaceutically acceptable excipient; c) at least one solubiliser in an amount from about 35% w/w to about 45% w/w; and d) at least one polar solvent in an amount from about 25% w/w to about 42% w/w, wherein the solubiliser and polar solvent are present in a ratio of from about 0.60:1 to about 1.8:1; and wherein the stable oral liquid pharmaceutical composition has a viscosity of from about 20 cps to about 1000 cps, and a density of from about 0.8 gm/cm³ to about 2 gm/cm³.

Some embodiments disclosed herein provide methods of treating pain in a human subject, the method comprising administering to the subject a stable oral liquid pharmaceutical composition, comprising a therapeutically effective amount of celecoxib, at least one solubiliser in amount from about 35% w/w to about 45% w/w, at least one polar solvent in amount from about 25% w/w to about 42% w/w, at least one medium chain glyceride, and at least one pharmaceutically acceptable excipient, wherein the stable oral liquid pharmaceutical composition is essentially free of precipitation inhibitors. In some embodiments, the pain is associated with migraine. In some embodiments, the therapeutically effective amount of celecoxib is sufficient to render the subject pain free within 2 hours of administering the stable oral liquid pharmaceutical composition. In some embodiments, the therapeutically effective amount of celecoxib is sufficient to lead to partial pain relief in the subject within 2 hours of administering the stable oral liquid pharmaceutical composition. In some embodiments, administering the stable oral liquid pharmaceutical composition leads to pain free at 2 hours in at least 25% of the human subjects being treated. In some embodiments, administering the stable oral liquid pharmaceutical composition leads to partial pain relief at 2 hours in at least 45% of the human subjects being treated. In some embodiments, administering the stable oral liquid pharmaceutical composition leads to an increase in the percentage of human subjects being treated being pain free at 2 hours that is at least 40% in comparison to the percentage of human subjects being treated with a placebo. In some embodiments, administering the stable oral liquid pharmaceutical composition leads to an increase in the percentage of human subjects being treated being partially relieved of pain at 2 hours that is at least 10% in comparison to the percentage of human subjects being treated with a placebo. In some embodiments, administering the stable oral liquid pharmaceutical composition leads to an increase in the percentage of human subjects being treated being pain free at 2 hours that is at least 10% in comparison to the percentage of human subjects being treated with a commercially available migraine pain treatment, such as VIOXX 25 (25 mg), VIOXX 50 (50 mg) and CAMBIA 50 (50 mg). In some embodiments, administering the stable oral liquid pharmaceutical composition leads to an increase in the percentage of human subjects being treated being partially relieved of pain at 2 hours that is at least 10% in comparison to the percentage of human subjects being treated with a commercially available migraine pain treatment, such as VIOXX 25 (25 mg), VIOXX 50 (50 mg) and CAMBIA 50 (50 mg).

Some embodiments disclosed herein provide uses of a stable oral liquid pharmaceutical composition disclosed in any of the embodiments throughout this application for the treatment of pain in a subject. In some embodiments, the stable oral liquid pharmaceutical composition comprises a therapeutically effective amount of celecoxib, at least one solubiliser in amount from about 35% w/w to about 45% w/w, at least one polar solvent in amount from about 25% w/w to about 42% w/w, at least one medium chain glyceride, and at least one pharmaceutically acceptable excipient, wherein the stable oral liquid pharmaceutical composition is essentially free of precipitation inhibitors. In some embodiments, the pain is associated with migraine. In some embodiments, the therapeutically effective amount of celecoxib is sufficient to render the subject pain free within 2 hours of administering the stable oral liquid pharmaceutical composition. In some embodiments, the therapeutically effective amount of celecoxib is sufficient to lead to partial pain relief in the subject within 2 hours of administering the stable oral liquid pharmaceutical composition. In some embodiments, administering the stable oral liquid pharmaceutical composition leads to pain free at 2 hours in at least 25% of the human subjects being treated. In some embodiments, administering the stable oral liquid pharmaceutical composition leads to partial pain relief at 2 hours in at least 45% of the human subjects being treated. In some embodiments, administering the stable oral liquid pharmaceutical composition leads to an increase in the percentage of human subjects being treated being pain free at 2 hours that is at least 40% in comparison to the percentage of human subjects being treated with a placebo. In some embodiments, administering the stable oral liquid pharmaceutical composition leads to an increase in the percentage of human subjects being treated being partially relieved of pain at 2 hours that is at least 10% in comparison to the percentage of human subjects being treated with a placebo. In some embodiments, administering the stable oral liquid pharmaceutical composition leads to an increase in the percentage of human subjects being treated being pain free at 2 hours that is at least 10% in comparison to the percentage of human subjects being treated with a commercially available migraine pain treatment, such as VIOXX 25 (25 mg), VIOXX 50 (50 mg) and CAMBIA 50 (50 mg). In some embodiments, administering the stable oral liquid pharmaceutical composition leads to an increase in the percentage of human subjects being treated being partially relieved of pain at 2 hours that is at least 10% in comparison to the percentage of human subjects being treated with a commercially available migraine pain treatment, such as VIOXX 25 (25 mg), VIOXX 50 (50 mg) and CAMBIA 50 (50 mg).

Some embodiments disclosed herein provide stable oral liquid pharmaceutical compositions of celecoxib comprising i. therapeutically effective amount of celecoxib, at least one solubiliser, at least one medium chain glyceride; and ii. polar solvent comprising mixture of ethanol and glycerin; wherein the composition falls within the shaded region of a phase diagram, as shown in FIG. 1, wherein boundaries of a stable composition are defined by shaded region or the region between the connecting lines between the six points (a, b, c, d, e and f), wherein the composition comprises about 1% to about 80% w/w celecoxib and correspond to a weight % ratio of base composition:ethanol:glycerin of 0.200:0.024:0.712 for a, 0.200:0.376:0.360 for b, 0.200:0.400:0.336 for c, 0.536:0.400:0.000 for d, 0.900:0.036:0.00 for e, and 0.900:0.00:0.036 for f. In some embodiments, said composition does not show any precipitation in Fasted-State Simulated Gastric Fluid (FaSSGF) at pH of 2.0, temperature of 37° C.±0.5° C. and under stirring at a speed of 50 rpm, when measured at 60 min. In some embodiments, the composition is essentially free of precipitation inhibitors selected from the group consisting of polyvinyl caprolactam-polyvinyl acetate-polyethylene glycol graft copolymer (SOLU-PLUS®), polyoxyethylene-polyoxypropylene block copolymers, pluronics, polyvinylpyrrolidone, and cellulosic polymers, including hydroxypropyl cellulose and hydroxypropyl methylcellulose. In some embodiments, the at least one solubiliser is polyethoxylated castor oil (available as KOLLIPHOR EL®), lauryl macrogolglyceride (available as GELUCIRE® 44/14), or a combination thereof. In some embodiments, the at least one medium chain glyceride is glyceryl tricaprylate/tricaprate (available as CAPTEX® 300), glyceryl monocaprylate (available as CAPMUL® MCM C8), or a combination thereof. In some embodiments, the at least one polar solvent is selected from the group consisting of propylene glycol, polyethylene glycols having a molecular weight between 400 and 1000, glycerin, C2 to C8 mono- and poly-alcohols (e.g., ethanol), C7 to C18 alcohols of linear or branched configuration, water and mixtures thereof. In some embodiments, the therapeutically effective amount of celecoxib comprises from about 1% to about 80% celecoxib by weight, based on the total weight of the composition. In some embodiments, the at least one solubiliser is present in an amount of from about 10% to about 70% by weight, based on the total weight of the composition. In some embodiments, a weight ratio of the at least one solubiliser to celecoxib varies from about 4.0:1.0 to about 20:1.0. In some embodiments, the at least one polar solvent is present in an amount of from about 20% to about 80% by weight, based on the total weight of the composition. In some embodiments, a weight ratio of the at least one solubiliser to the at least one polar solvent varies from about 0.60:1.00 to about 1.8:1.00. In some embodiments, the at least one medium chain glyceride is present in an amount of from about 5% to about 75% by weight, based on the total weight of the composition. In some embodiments, the composition has a mean oil droplet size of not more than 500 nm, when tested in 250 ml of Fasted-State Simulated Gastric Fluid (FaSSGF) at pH of 2.0, temperature of 37° C.±0.5° C. and under stirring at a speed of 50 rpm. In some embodiments, the composition has a viscosity of from about 20 cps to about 1000 cps. In some embodiments, the composition has a density of from about 0.8 gm/cm$^3$ to about 2 gm/cm$^3$. In some embodiments, the composition has a transmittance of at least 40%. In some embodiments, the composition has a pH of from about 3 to about 7. In some embodiments, the therapeutically effect amount of celecoxib is at least about 40% less than conventional celecoxib compositions such as CELEBREX® 400 mg oral capsules. In some embodiments, the therapeutically effect amount of celecoxib is about 240 mg. In some embodiments, the therapeutically effect amount of celecoxib is at least about 55% less than conventional celecoxib compositions such as CELEBREX® 400 mg oral capsules. In some embodiments, the therapeutically effect amount of celecoxib is about 180 mg. In some embodiments, the therapeutically effect amount of celecoxib is at least about 70% less than conventional celecoxib compositions such as CELEBREX® 400 mg oral capsules. In some embodiments, the therapeutically effect amount of celecoxib is about 120 mg. In some embodiments, the stable oral liquid pharmaceutical compositions, which upon oral administration to a human subject under fasting conditions, provides at least one of the following pharmacokinetic parameters:

$AUC_{(0-15\ min)}$ from about 10 ng·h/mL to about 80 ng·h/mL;

$AUC_{(0-30\ min)}$ from about 80 ng·h/mL to about 400 ng·h/mL;

$AUC_{(0-1\ hr)}$ from about 400 ng·h/mL to about 1500 ng·h/mL;

$AUC_{(0-2\ hr)}$ from about 1000 ng·h/mL to about 4000 ng·h/mL;

$AUC_{(0-t)}$ of at least about 2000 ng·h/mL;

$AUC_{(0-\infty)}$ of at least about 2000 ng·h/mL; and $T_{lag}$ of not more than 8 minutes.

In some embodiments, the stable oral liquid pharmaceutical compositions comprise: a) a therapeutically effective amount of celecoxib; b) at least one pharmaceutically acceptable excipient; c) at least one solubiliser in an amount from about 35% w/w to about 45% w/w; and d) at least one polar solvent in an amount from about 25% w/w to about 42% w/w, wherein the solubiliser and polar solvent are present in a ratio of from about 0.60:1 to about 1.8:1; and wherein the stable oral liquid pharmaceutical composition has a viscosity of from about 20 cps to about 1000 cps, and a density of from about 0.8 gm/cm$^3$ to about 2 gm/cm$^3$.

DETAILED DESCRIPTION

Definitions

Figure 1:
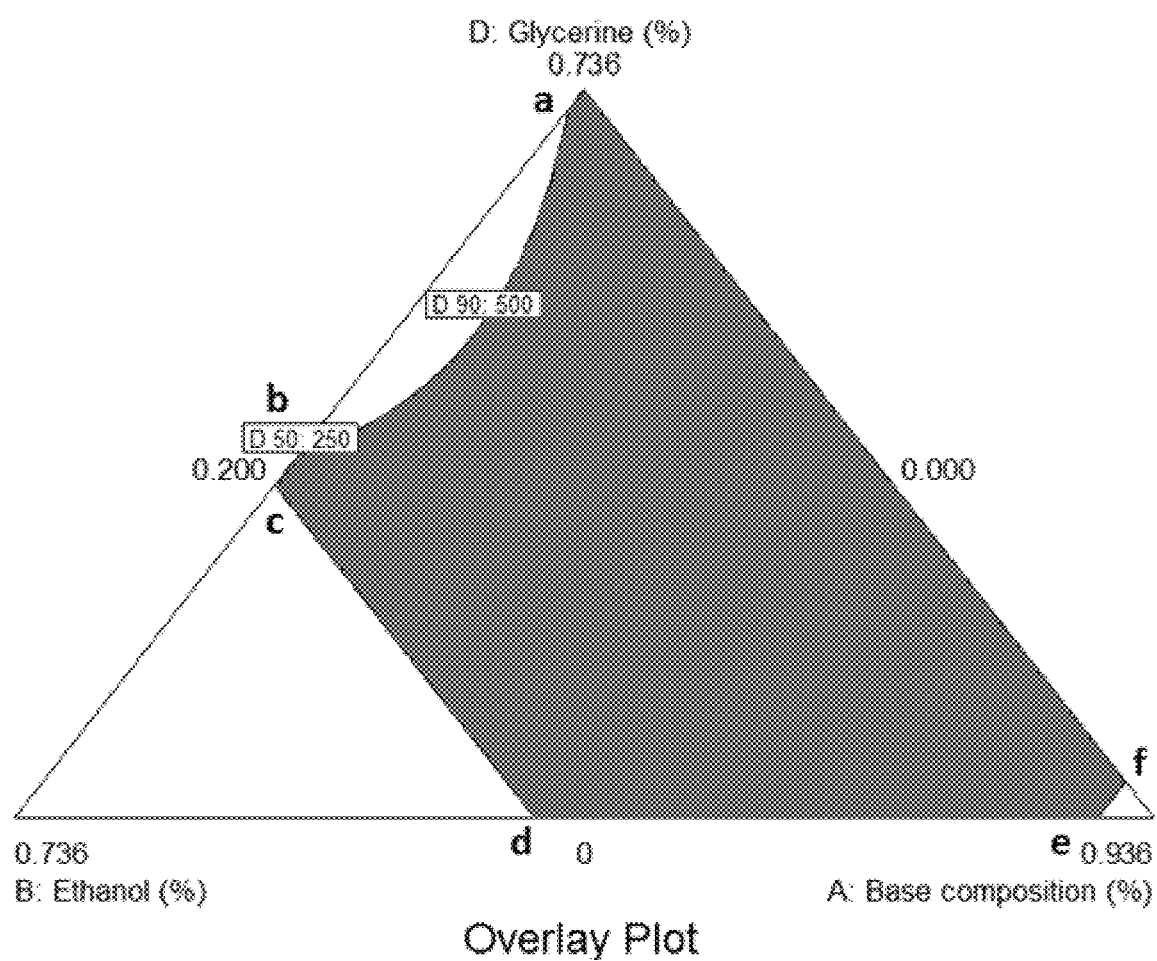
FIG. 1 shows a ternary phase diagram. The shaded region is "stable composition region A" and is formed by connecting lines between points (a, b, c, d, e and f).

Unless otherwise defined, all technical and scientific terms used herein have the same meaning as commonly understood by one of ordinary skill in the art.

As used herein, "comprising" is "open ended" and means the elements recited, or their equivalent in structure or function, plus any other element or elements which are not recited. The terms "having" and "including" are also to be construed as open ended unless the context suggests otherwise. All the ranges recited herein include the endpoints, including those that recite a range "between" two values.

The terms "a" and "the" as used herein are understood to encompass the plural as well as the singular or otherwise clearly mentioned wherever needed. For example, reference to "an excipient" includes reference to one or more of such excipients, and reference to "the carrier" includes reference to one or more of such carriers.

The terms such as 'about', 'up to', 'generally', 'substantially' and the like are to be construed as modifying a term or value such that it is not an absolute. Such terms will be defined by the circumstances and the terms that they modify as those terms are understood by those of skilled in the art. This includes, at very least, the degree of expected experimental error, technical error and instrumental error for a given experiment, technique or an instrument used to measure a value. The term "about" is used to provide flexibility to a numerical range endpoint by providing that a given value may be "a little above" or "a little below" the endpoint. As used herein, the term "about" means a slight variation of the value specified, preferably within 10% of the value specified. Nevertheless, the term "about" can mean a higher tolerance of variation depending on for instance the experimental technique used. Said variations of a specified value are understood by the skilled person and are within the context of the present invention. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, 5, or 6, individually. This same principle applies to ranges reciting only one numerical value as a minimum or a maximum.

As used herein, "free of" or "essentially free of" a particular compound or compositions or excipients refer to the absence of any separately added portion of the referenced compound or composition or excipients. The term "free of" or "essentially free of" means that there is less than 1% w/w of a particular compound or compositions, or excipients, wherein the amount present does not impart any functional value to the composition.

"Celecoxib" as used herein encompasses base form as well as its pharmaceutically acceptable salts, complexes, polymorphs, hydrates, solvates, enantiomers or racemates. The solid state form of celecoxib used in the composition of the present application is not critical. For example, celecoxib can be amorphous or crystalline.

The term "pharmaceutically acceptable salts" as used herein includes those salts which are, within the scope of sound medical judgment, suitable for use in contact with the tissues of humans and lower animals without undue toxicity, irritation, allergic response and the like, which are well known in the art. The salts can be prepared in situ during the final isolation and purification of the compounds of the invention, or separately by reacting the pharmaceutically active substance, having a freebase function, with a suitable organic acid or inorganic acid.

As used herein, an "effective amount" or a "therapeutically effective amount" of a drug refers to a non-toxic, but sufficient amount of the drug, to achieve therapeutic results in treating a condition for which the drug is known to be effective. In this instance, an effective amount is an amount of celecoxib which is sufficient to treat pain in a patient in need thereof which is to say to provide some measure of analgesia to reduce at least the patient's perception of pain.

The term "liquid composition" refers to a liquid composition that is ingested with or without further mixing with aqueous or suitable media before oral administration.

The term "stable composition(s)" as used herein, refers to a composition that does not show any precipitation in Fasted-State Simulated Gastric Fluid (FaSSGF) at pH 2.0, temperature of 37° C.±0.5° C. and under stirring at a speed of 50 rpm at least for 60 minutes. Also the term "stable composition(s)" refers to a composition which upon subjected to stability evaluation at 40° C. and 75% RH (relative humidity) or 25° C. and 60% RH (relative humidity), is substantially free of impurities, or comprises not more than 5% impurities, or comprises impurities levels which are acceptable by regulatory bodies such as US FDA.

The term "precipitation inhibitor" as used herein refers to a pharmaceutically acceptable excipient that prevents the precipitation of celecoxib when orally administered to a human subject, or when tested in a simulated gastric fluid, e.g., Fasted-State Simulated Gastric Fluid (FaSSGF), pH 2.0, at 37° C. under stirring condition. Examples of precipitation inhibitors include: polyvinyl caprolactam-polyvinyl acetate-polyethylene glycol graft copolymer (SOLUPLUS®), polyoxyethylene-polyoxypropylene block copolymers, pluronics, polyvinylpyrrolidone, and cellulosic polymers, including hydroxypropyl cellulose and hydroxypropyl methylcellulose. Non-cellulosic polymers that inhibit precipitation may also be included among the possible precipitation inhibitors.

The term "Fasted-State Simulated Gastric Fluid (FaSSGF)" as used herein, refers to a standard in vitro assay that is used to simulate the environment of the fasted-state gastric fluid for evaluation of the stability (or solubility or suitability) of drug formulations for oral delivery. The composition of FaSSG is 0.1N HCl with 0.05% SLS and pH adjusted with NaOH/HCl.

The term "conventional celecoxib oral composition" or "conventional composition" as used herein, refers to oral celecoxib capsules marketed under the brand name CELEBREX® by G.D. Searle LLC in US or its pharmaceutical equivalents or its therapeutic equivalents or later approved drugs which are designated as AB rated by US FDA as per Approved Drug Products with Therapeutic Equivalence Evaluations (34th edition) or drugs obtained marketing approval by US FDA through Abbreviated New Drug Application (ANDA) filing by establishing bioequivalence to such Product". In some embodiments CELEBREX® includes its US FDA approved therapeutic or pharmaceutical equivalents. CELEBREX® is a Trademark registered and owned by G.D. Searle LLC (Division of Pfizer Inc. NY), NY 10017, USA. In some other embodiments "conventional celecoxib oral composition" or "conventional composition" also includes oral celecoxib capsules marketed under the brand name ZYCEL® by Zydus Cadila, Zydus Tower, Ahmedabad, India. CELEBREX® is available in the strengths of 50 mg, 100 mg, 200 mg and 400 mg celecoxib containing oral capsules. ZYCEL® is available in the strengths of 100 mg and 200 mg celecoxib containing oral capsules.

As used herein the term "pain" refers to pain as recited herein acute pain, migraine pain, cluster headache, neuropathic pain, post-operative pain, chronic lower back pain, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post-partum pain, angina pain, and genitourinary tract-related pain including cystitis, arthritis pain, inflammation, osteoarthritis, juvenile rheumatoid arthritis, ankylosing spondylitis and primary dysmenorrhea.

As used herein the term "treating" includes treatment and/or prophylaxis of a physical and/or mental condition or amelioration or elimination of the developed condition once it has been established or alleviation of the characteristic symptoms of such condition.

As used herein, the term "mammal" shall refer to the mammalian class of higher vertebrates. The term "mammal" includes, but is not limited to, a human.

Stable Oral Liquid Pharmaceutical Compositions

In some embodiments, the present application provides stable oral liquid pharmaceutical compositions comprising a therapeutically effective amount of celecoxib. In some embodiments, the stable oral liquid pharmaceutical compositions disclosed herein comprise at least one solubiliser, at least one medium chain glyceride, at least one polar solvent, and/or at least one pharmaceutically acceptable excipient.

Without being bound by a particular theory, it is contemplated that the stable oral liquid pharmaceutical compositions disclosed herein show improved solubilization characters, for example, when administered orally to a human subject. In some embodiments, the stable oral liquid pharmaceutical compositions disclosed herein do not show any precipitation in a simulated gastric fluid (GSF) for a prolonged time. For example, the stable oral liquid pharmaceutical compositions disclosed herein do not show any precipitation in a simulated gastric fluid (GSF) for at least 10 min, at least 20 min, at least 30 min, at least 40 min, at least 50 min, at least 60 min, at least 90 min, at least 2 hr, at least 3 hr, at least 4 hr, at least 5 hr, at least 6 hr, at least 12 hr, at least 24 hr, or longer. In some embodiments, the stable oral liquid pharmaceutical compositions disclosed herein do not show any precipitation in a Fasted-State Simulated Gastric Fluid (FaSSGF) for a prolonged time. For example, the stable oral liquid pharmaceutical compositions disclosed herein do not show any precipitation in a Fasted-State Simulated Gastric Fluid (FaSSGF) for at least 10 min, at least 20 min, at least 30 min, at least 40 min, at least 50 min, at least 60 min, at least 90 min, at least 2 hr, at least 3 hr, at least 4 hr, at least 5 hr, at least 6 hr, at least 12 hr, at least 24 hr, or longer.

In some embodiments, the stable oral liquid pharmaceutical compositions disclosed herein do not show any precipitation in a low pH environment. For example, the stable oral liquid pharmaceutical compositions disclosed herein do not show any precipitation in a Fasted-State Simulated Gastric Fluid (FaSSGF) at pH 1.0-6.0 for at least 10 min, at least 20 min, at least 30 min, at least 40 min, at least 50 min, at least 60 min, at least 90 min, at least 2 hr, at least 3 hr, at least 4 hr, at least 5 hr, at least 6 hr, at least 12 hr, at least 24 hr, or longer. In some embodiments, the stable oral liquid pharmaceutical compositions disclosed herein do not show any precipitation in a Fasted-State Simulated Gastric Fluid (FaSSGF) at pH 1.0-5.0 for at least 10 min, at least 20 min, at least 30 min, at least 40 min, at least 50 min, at least 60 min, at least 90 min, at least 2 hr, at least 3 hr, at least 4 hr, at least 5 hr, at least 6 hr, at least 12 hr, at least 24 hr, or longer. In some embodiments, the stable oral liquid pharmaceutical compositions disclosed herein do not show any precipitation in a Fasted-State Simulated Gastric Fluid (FaSSGF) at pH 1.0-4.0 for at least 10 min, at least 20 min, at least 30 min, at least 40 min, at least 50 min, at least 60 min, at least 90 min, at least 2 hr, at least 3 hr, at least 4 hr, at least 5 hr, at least 6 hr, at least 12 hr, at least 24 hr, or longer. In some embodiments, the stable oral liquid pharmaceutical compositions disclosed herein do not show any precipitation in a Fasted-State Simulated Gastric Fluid (FaSSGF) at pH 1.0-3.0 for at least 10 min, at least 20 min, at least 30 min, at least 40 min, at least 50 min, at least 60 min, at least 90 min, at least 2 hr, at least 3 hr, at least 4 hr, at least 5 hr, at least 6 hr, at least 12 hr, at least 24 hr, or longer. In some embodiments, the stable oral liquid pharmaceutical compositions disclosed herein do not show any precipitation in a Fasted-State Simulated Gastric Fluid (FaSSGF) at pH 2.0-3.0 for at least 10 min, at least 20 min, at least 30 min, at least 40 min, at least 50 min, at least 60 min, at least 90 min, at least 2 hr, at least 3 hr, at least 4 hr, at least 5 hr, at least 6 hr, at least 12 hr, at least 24 hr, or longer. In some embodiments, the stable oral liquid pharmaceutical compositions disclosed herein do not show any precipitation in a Fasted-State Simulated Gastric Fluid (FaSSGF) at pH 2.0 for at least 10 min, at least 20 min, at least 30 min, at least 40 min, at least 50 min, at least 60 min, at least 90 min, at least 2 hr, at least 3 hr, at least 4 hr, at least 5 hr, at least 6 hr, at least 12 hr, at least 24 hr, or longer.

Without being bound by any particular theory, the stable oral liquid pharmaceutical compositions disclosed herein are essentially free of any precipitation inhibitors. In some embodiments, the stable oral liquid pharmaceutical compositions disclosed herein are completely free of any precipitation inhibitors. In some embodiments, the celecoxib composition of present application is essentially free of precipitation inhibitors such as, polyoxyethylene-polyoxypropylene block copolymers, pluronics, polyvinylpyrrolidone, hydroxypropyl cellulose and hydroxypropyl methylcellulose. In some embodiments, the celecoxib compositions of the present application are essentially free of precipitation inhibitors including: polyvinyl caprolactam-polyvinyl acetate-polyethylene glycol graft copolymer (SOLUPLUS®), polyoxyethylene-polyoxypropylene block copolymers, pluronics, polyvinylpyrrolidone, cellulosic polymers, including hydroxypropyl cellulose and hydroxypropyl methylcellulose, and non-cellulosic polymers.

In some embodiments, the present application provides a stable oral pharmaceutical composition comprising therapeutically effective amount of celecoxib, wherein said composition provides mean oil droplet size of no more than 500 nm, when tested in 250 ml of Fasted-State Simulated Gastric Fluid (FaSSGF) at pH of 2.0, temperature of 37° C.±0.5° C. and under stirring at a speed of 50 rpm.

In some embodiments, the present application provides a stable oral pharmaceutical composition comprising therapeutically effective amount of celecoxib, wherein said composition does not show any precipitation in the dissolution medium or Fasted-State Simulated Gastric Fluid (FaSSGF) at pH of 2.0, temperature of 37° C.±0.5° C. and under stirring at a speed of 50 rpm, when measured at 30 min or 60 min or 90 min or 120 minutes or 180 minutes or 240 minutes time points; and said composition is essentially free of precipitation inhibitors such as, polyoxyethylene-polyoxypropylene block copolymers, pluronics, polyvinylpyrrolidone, hydroxypropyl cellulose and hydroxypropyl methylcellulose.

In some embodiments, the present application provides a stable oral liquid pharmaceutical composition comprising therapeutically effective amount of celecoxib, wherein said composition does not show any precipitation in Fasted-State Simulated Gastric Fluid (FaSSGF) at pH of 2.0, temperature of 37° C.±0.5° C. and under stirring at a speed of 50 rpm, when measured at 30 min or 60 min or 90 min or 120 minutes or 180 minutes or 240 minutes time points; and said composition is essentially free of precipitation inhibitors such as, polyoxyethylene-polyoxypropylene block copolymers, pluronics, polyvinylpyrrolidone, hydroxypropyl cellulose and hydroxypropyl methylcellulose.

In some embodiments, the present application provides a stable oral pharmaceutical composition comprising therapeutically effective amount of celecoxib, at least one solubiliser, at least one medium chain glyceride, at least one polar solvent and at least one pharmaceutically acceptable excipients, wherein said composition does not show any precipitation in Fasted-State Simulated Gastric Fluid (FaSSGF) at pH of 2.0, temperature of 37° C.±0.5° C. and under stirring at a speed of 50 rpm, when measured at 30 min or 60 min or 90 min or 120 minutes or 180 minutes or 240 minutes time points; and said composition is essentially free of precipitation inhibitors such as, polyoxyethylene-polyoxypropylene block copolymers, pluronics, polyvinylpyrrolidone, hydroxypropyl cellulose and hydroxypropyl methylcellulose.

In some embodiments, the present application provides a stable oral liquid pharmaceutical composition comprising therapeutically effective amount of celecoxib, at least one solubiliser, at least one medium chain glyceride, at least one polar solvent and at least one pharmaceutically acceptable excipients, wherein said composition does not show any precipitation in Fasted-State Simulated Gastric Fluid (FaSSGF) at pH of 2.0, temperature of 37° C.±0.5° C. and under stirring at a speed of 50 rpm, when measured at 30 min or 60 min or 90 min or 120 minutes or 180 minutes or 240 minutes time points; and said composition is essentially free of precipitation inhibitors such as, polyoxyethylene-polyoxypropylene block copolymers, pluronics, polyvinylpyrrolidone, hydroxypropyl cellulose and hydroxypropyl methylcellulose.

The oral pharmaceutical celecoxib composition of present application can be formulated in the form of a solution, suspension, emulsion or liquid mixture.

Medium Chain Glycerides

In some embodiments, the stable oral liquid pharmaceutical compositions of the present application further comprise at least one medium chain glycerides. As used herein, a medium chain glyceride can refer to a medium chain mono-glyceride, a medium chain bi-glyceride, and/or a medium chain triglyceride (MCT). MCTs are triglycerides whose fatty acids have an aliphatic tail of 6-12 carbon atoms. MCTs are composed of a glycerol backbone and three fatty acids. In the case of MCTs, 2 or 3 of the fatty acid chains attached to glycerol are medium-chain in length. Exemplary medium chain fatty acids include Caproic acid, Caprylic acid, Capric acid, Lauric acid, etc. It would be appreciated that the medium chain glycerides, such as MCTs, can improve the solubility of the stable oral liquid pharmaceutical compositions disclosed herein when orally administered to the human subject, or in a simulated gastric fluid, e.g., Fasted-State Simulated Gastric Fluid (FaSSGF).

The medium chain glyceride may be present in the stable oral liquid pharmaceutical compositions disclosed herein in a variety of concentrations. For example, the stable oral liquid pharmaceutical compositions disclosed herein can comprise a medium chain glyceride of at least 10% by weight, at least 20% by weight, at least 30% by weight, at least 40% by weight, at least 50% by weight, at least 60% by weight, at least 70% by weight, at least 80% by weight, at least 90% by weight, or a percentage between any two of the above values, based on the total weight of the composition.

In some embodiments, the celecoxib compositions of present application comprises of at least one medium chain glyceride in an amount of from about 5% to about 75% by weight, or from about 5% to about 65% by weight, or from about 5% to about 55% by weight, or from about 5% to about 45% by weight, or from about 5% to about 35% by weight, based on the total weight of the composition.

In some embodiments, the celecoxib compositions of present application further comprises of medium chain having at least one medium chain mono- or di- or tri-glyceride or mixtures thereof.

Suitable examples of medium chain mono- or di or tri-glyceride (MCT) used in the compositions of the present application are well known in the art. The non-limiting examples of medium chain mono- or di or tri-glyceride (MCT) include, but are not limited to, both even and odd fatty acids, such as fatty acids containing C4 (butyric acid, butanoic acid), C5 (valeric acid), C6 (caproic acid, hexanoic acid), C7 (heptanoic acid), C8 (caprylic acid, octanoic acid), C9 (pelargonic acid), C10 (capric acid, decanoic acid), C11 (undecanoic acid) or C12 (lauric acid, dodecanoic acid) and both even and odd fatty acid (containing two to twelve carbon atoms) ester with glycerol such as glyceryl monocaprylate, glyceryl di-caprylate, propylene glycol heptanoate, glyceryl monocaprate, glyceryl caprylate/caprate, medium chain mono- and diglycerides available as Capmul MCM®, propylene glycol monocaprylate and di-caprylate, glyceryl tricaprylate, glycerol tricaprylate/caprate, glyceryl tricaprylate/tricaprate, glyceryl tricaprylate/tricaprate PEG-8 Caprylic/Capric Glycerides, Further the medium chain glyceride component may be a naturally occurring mono- or di or tri-glycerides containing composition, such as obtained from butterfat, soy oil, coconut oil and the like.

In some embodiments, the celecoxib compositions of present application comprises of at least one medium chain glycerides selected from the group of Lauroyl macrogolglycerides, Glyceryl Monocaprylate, Glyceryl Tricaprylate/Tricaprate or mixtures thereof.

Alternatively, said glyceride component may comprise at least one industrially prepared glycerides or a mixture of naturally occurring and industrially prepared glycerides. Said glyceride may be prepared by interesterification of C4 to C12 chain fatty acids such as caprylocaproyl macrogol-8 glycerides.

Polar Solvents

In some embodiments, the stable oral liquid pharmaceutical compositions of the present application further comprise at least one polar solvents. Without being bound by any particular theory, the addition of polar solvent in the compositions of celecoxib as per present application additionally helps in delaying the onset of precipitation time. In some embodiments, the onset of precipitation is delayed at least about 1-10 hours compared to the compositions of celecoxib which are substantially free of polar solvent. In some embodiments, the polar solvent can delay the onset of precipitation time for at least about 1 hour, at least about 2 hours, at least about 3 hours, at least about 4 hours, at least about 5 hours, at least about 6 hours, or more.

Suitable examples of polar solvent that can be used in the present application are selected from the group comprising propylene glycol, polyethylene glycols having a molecular weight between 400 and 1000, glycerin, $C_2$ to $C_8$ mono- and poly-alcohols such as ethanol, etc., $C_7$ to $C_{18}$ alcohols of linear or branched configuration, water and any combination thereof.

The polar solvent may be present in the stable oral liquid pharmaceutical compositions disclosed herein in a variety of concentrations. For example, the stable oral liquid pharmaceutical compositions disclosed herein can comprise a polar solvent of at least 10% by weight, at least 20% by weight, at least 30% by weight, at least 40% by weight, at least 50% by weight, at least 60% by weight, at least 70% by weight, at least 80% by weight, at least 90% by weight, or a percentage between any two of the above values, based on the total weight of the composition.

In some embodiments, the celecoxib compositions of present application comprises of polar solvent is in an amount of from about 20% to about 80% by weight, or from about 20% to about 70% by weight or from about 20% to about 60% by weight, or from about 20% to about 50% by weight, or from about 20% to about 40% by weight, based on the total weight of the composition.

Solubilisers

In some embodiments, the stable oral liquid pharmaceutical compositions of the present application comprises of at least one solubilisers selected from the group of nonionic, anionic, cationic and zwitterionic surfactants or mixtures thereof.

Suitable non-limiting examples of the solubiliser(s) used in the compositions of the present application includes, but not limited to, polyethoxylated fatty acids like esters of lauric acid, oleic acid, and stearic acid, PEG-fatty acid diesters like PEG-20 dilaurate, PEG-fatty acid mono- and di-ester mixtures, alcohol-oil transesterification products like PEG-35 castor oil, Polyoxy 35 castor oil, polyoxyl 40 hydrogenated castor oil, etc., polyglycerized fatty acids like polyglyceryl oleate, etc., propylene glycol fatty acid esters like propylene glycol monolaurate etc, mixtures of propylene glycol esters-glycerol esters like oleic acid esters of propylene glycol and glycerol, etc., sterol and sterol derivatives like PEG-24 cholesterol ether etc, polyethylene glycol sorbitan fatty acid esters like PEG-20 sorbitan monolaurate etc, polyethylene glycol alkyl ethers like PEG-3 oleyl ether, etc., sugar esters like sucrose monopalmitate etc, polyethylene glycol alkyl phenols like Octoxynol-1 etc, sorbitan fatty acid esters like sorbitan monolaurate, lower alcohol fatty acid esters like ethyl oleate, etc., anionic surfactants include fatty acid salts and bile salts. Additional exemplary solubilisers include, but are not limited to: polyoxyethylene alkylethers; polyethylene glycol fatty acid esters; polyethylene glycol glycerol fatty acid esters; polyoxyethylene sorbitan fatty acid esters; polyglycerol fatty acid esters; polyoxyethylene glycerides; polyoxyethylene vegetable oils; polyoxyethylene hydrogenated vegetable oils, alkylglucosides; alkylmaltosides; alkylthioglucosides; lauryl macrogolglycerides Ionic surfactants include sodium oleate, sodium lauryl sulfate, sodium lauryl sarcosinate, sodium dioctyl sulfosuccinate, sodium cholate, and sodium taurocholate; Gelucire® 44/14, etc.

In some embodiments, the celecoxib compositions of present application comprises at least one solubilisers selected from the group consisting of, glycerol polyethylene glycol ricinoleate, macrogolglycerol ricinoleate Ph. Eur., polyoxyl 35 castor Oil lauroyl polyoxyl-32 glycerides, lauroyl macrogol-32 glycerides, polyoxyl 40 hydrogenated castor oil, Polyoxy 35 castor oil, PEG-40 Hydrogenated Castor Oil, or mixtures thereof.

The at least one solubilisers may be present in the stable oral liquid pharmaceutical compositions disclosed herein in a variety of concentrations. For example, the stable oral liquid pharmaceutical compositions disclosed herein can comprise at least one solubilisers of at least 10% by weight, at least 20% by weight, at least 30% by weight, at least 40% by weight, at least 50% by weight, at least 60% by weight, at least 70% by weight, at least 80% by weight, at least 90% by weight, or a percentage between any two of the above values, based on the total weight of the composition. In some embodiments, the celecoxib composition of present application comprises of at least one solubilisers in an amount of from about 10% to about 70% by weight, or from about 20% to about 60% by weight, or from about 20% to about 50% by weight, or from about 30% to about 40% by weight, based on the total weight of the composition.

In certain aspects of the above embodiments, the celecoxib composition of present application comprises solubiliser and polar solvent in a weight ratio of from about 0.60:1.00 to about 1.8:1.00.

In another aspect of above embodiments, the present application provides a stable liquid oral pharmaceutical composition of celecoxib comprising therapeutically effective amount of celecoxib, at least one solubiliser and at least one polar solvent, wherein said composition comprises solubiliser and polar solvent in weight ratio of from about 0.60:1.00 to about 1.8:1.00.

In certain aspects of the above embodiments, the present application provides a stable oral liquid pharmaceutical composition of celecoxib comprising therapeutically effective amount of celecoxib, at least one solubiliser, at least one polar solvent and at least one pharmaceutically acceptable excipient, wherein said composition comprises solubiliser and polar solvent in weight ratio of from about 0.60:1.00 to about 1.8:1.00.

In an aspect of the above embodiments, the compositions of the present application comprises celecoxib in an amount of from about 1% to about 80% by weight, or from about 2% to about 70% by weight, or from about 2% to about 50% by weight, or from about 20% to about 40% by weight, or from about 2% to about 8% by weight, based on the total weight of the composition.

In some embodiments, the present application provides a stable oral liquid oral pharmaceutical composition of celecoxib comprising, therapeutically effective amount of celecoxib, at least one solubiliser and at least one pharmaceutically acceptable excipients, wherein said composition comprises solubiliser and celecoxib in weight ratio of from about 4.0:1.0 to about 20:1.0.

In some embodiments, the celecoxib compositions of present application comprises of at least one medium chain glyceride and celecoxib in a weight ratio of from about 2.0:1.0 to about 20:1.0. In some embodiments, compositions of present application comprises of at least one medium chain glyceride and celecoxib in a weight ratio of from about 2.0:1.0 to about 10.0:1.0.

In some embodiments, the celecoxib compositions of present application comprises of at least one solubiliser and at least one medium chain glyceride in a ratio of from about 0.05:1.0 to about 20:1.0. In some embodiment, celecoxib composition of present application comprises of at least one solubiliser and at least one medium chain glyceride in a ratio of from about 0.05:1.0 to about 10.0:1.0.

In some embodiments, the celecoxib composition of present application comprises of at least one solubiliser and celecoxib in a weight ratio of from about 4.0:1.0 to about 20:1.0.

In some embodiments, the present application provides a pharmaceutical composition of celecoxib comprising:
 a. therapeutically effective amount of celecoxib;
 b. at least one solubiliser in amount from about 35% w/w to about 45% w/w;
 c. at least one polar solvent in amount from about 25% w/w to about 42% w/w; and
 d. at least one pharmaceutically acceptable excipient,
wherein said solubiliser and polar solvent are present in the ratio of from about 0.60:1.00 to about 1.8:1.00 and does not show any precipitation in Fasted-State Simulated Gastric Fluid (FaSSGF) at pH 2.0, temperature of 37° C.±0.5° C. and under stirring at a speed of 50 rpm at least for 60 minutes.

Improved Pharmacokinetic Parameters

The stable oral liquid pharmaceutical compositions disclosed herein can have a variety of pharmacokinetic parameters. In some embodiments, the stable oral liquid pharmaceutical compositions disclosed herein can have an improved pharmacokinetic parameter in comparison to a conventional celecoxib oral composition, such as $AUC_{(0-15\ min)}$, $AUC_{(0-30\ min)}$, $AUC_{(0-1\ hr)}$, $AUC_{(0-2\ hr)}$, $AUC_{(0-t)}$, $AUC_{(0-\infty)}$, $T_{lag}$, $T_{max}$, etc.

In some embodiments, the stable oral liquid pharmaceutical compositions disclosed herein, upon oral administration to a human subject under fasting conditions provides $T_{lag}$ of not more than 60 minutes, not more than 30 minutes, not more than 20 minutes, not more than 10 minutes, not more than 8 minutes, not more than 6 minutes, not more than 5 minutes, not more than 4 minutes, not more than 3 minutes, not more than 2 minutes, not more than 1 minutes, or less. In some embodiments, the stable oral liquid pharmaceutical compositions disclosed herein, upon oral administration to a human subject under fasting conditions provides $T_{max}$ of less than about 120 minutes, less than about 90 minutes, less than about 80 minutes, less than about 70 minutes, less than about 60 minutes, less than about 50 minutes, less than about 40 minutes, less than about 30 minutes, less than about 20 minutes, or less. In some embodiments, the stable oral liquid pharmaceutical compositions disclosed herein, upon oral administration to a human subject under fasting conditions provides $AUC_{(0-15\ min)}$ of at least about 1 ng·h/mL, at least about 2 ng·h/mL, at least about 5 ng·h/mL, at least about 10 ng·h/mL, at least about 20 ng·h/mL, at least about 30 ng·h/mL, at least about 40 ng·h/mL, at least about 50 ng·h/mL, at least about 100 ng·h/mL, at least about 200 ng·h/mL, or more, or a range between any two of the above values. In some embodiments, the stable oral liquid pharmaceutical compositions disclosed herein, upon oral administration to a human subject under fasting conditions provides $AUC_{(0-30\ min)}$ of at least about 10 ng·h/mL, at least about 20 ng·h/mL, at least about 30 ng·h/mL, at least about 40 ng·h/mL, at least about 50 ng·h/mL, at least about 60 ng·h/mL, at least about 70 ng·h/mL, at least about 80 ng·h/mL, at least about 90 ng·h/mL, at least about 100 ng·h/mL, at least about 200 ng·h/mL, at least about 500 ng·h/mL, or more, or a range between any two of the above values. In some embodiments, the stable oral liquid pharmaceutical compositions disclosed herein, upon oral administration to a human subject under fasting conditions provides $AUC_{(0-1\ hr)}$ of at least about 100 ng·h/mL, at least about 200 ng·h/mL, at least about 300 ng·h/mL, at least about 400 ng·h/mL, at least about 500 ng·h/mL, at least about 600 ng·h/mL, at least about 700 ng·h/mL, at least about 800 ng·h/mL, at least about 900 ng·h/mL, at least about 1000 ng·h/mL, at least about 1500 ng·h/mL, at least about 2000 ng·h/mL, at least about 3000 ng·h/mL, at least about 4000 ng·h/mL, or more, or a range between any two of the above values. In some embodiments, the stable oral liquid pharmaceutical compositions disclosed herein, upon oral administration to a human subject under fasting conditions provides $AUC_{(0-2\ hr)}$ of at least about 500 ng·h/mL, at least about 600 ng·h/mL, at least about 700 ng·h/mL, at least about 800 ng·h/mL, at least about 900 ng·h/mL, at least about 1000 ng·h/mL, at least about 1500 ng·h/mL, at least about 2000 ng·h/mL, at least about 3000 ng·h/mL, at least about 4000 ng·h/mL, at least about 5000 ng·h/mL, at least about 6000 ng·h/mL, at least about 7000 ng·h/mL, at least about 8000 ng·h/mL, or more, or a range between any two of the above values. In some embodiments, the stable oral liquid pharmaceutical compositions disclosed herein, upon oral administration to a human subject under fasting conditions provides $AUC_{(0-t)}$ of at least about 500 ng·h/mL, at least about 600 ng·h/mL, at least about 700 ng·h/mL, at least about 800 ng·h/mL, at least about 900 ng·h/mL, at least about 1000 ng·h/mL, at least about 1500 ng·h/mL, at least about 2000 ng·h/mL, at least about 3000 ng·h/mL, at least about 4000 ng·h/mL, at least about 5000 ng·h/mL, at least about 6000 ng·h/mL, at least about 7000 ng·h/mL, at least about 8000 ng·h/mL, or more, or a range between any two of the above values. In some embodiments, the stable oral liquid pharmaceutical compositions disclosed herein, upon oral administration to a human subject under fasting conditions provides $AUC_{(0-\infty)}$ of at least about 500 ng·h/mL, at least about 600 ng·h/mL, at least about 700 ng·h/mL, at least about 800 ng·h/mL, at least about 900 ng·h/mL, at least about 1000 ng·h/mL, at least about 1500 ng·h/mL, at least about 2000 ng·h/mL, at least about 3000 ng·h/mL, at least about 4000 ng·h/mL, at least about 5000 ng·h/mL, at least about 6000 ng·h/mL, at least about 7000 ng·h/mL, at least about 8000 ng·h/mL, or more, or a range between any two of the above values.

In some embodiments, the stable oral liquid pharmaceutical compositions disclosed herein, upon oral administration to a human subject under fasting conditions have a release rate of no less than 50%, no less than 60%, no less than 70%, no less than 80%, no less than 90%, at a period of 10 minutes. In some embodiments, the stable oral liquid pharmaceutical compositions disclosed herein, upon oral administration to a human subject under fasting conditions have a release rate of no less than 50%, no less than 60%, no less than 70%, no less than 80%, no less than 90%, at a period of 15 minutes. In some embodiments, the stable oral liquid pharmaceutical compositions disclosed herein have a release rate of no less than 50%, no less than 60%, no less than 70%, no less than 80%, no less than 90%, at a period of 10 minutes in 900 ml of 0.01N HCl with 0.5% sodium lauryl sulphate (SLS), when tested in a USP Type 2 apparatus with sinkers at 50 rpm and 37° C. In some embodiments, the stable oral liquid pharmaceutical compositions disclosed herein have a release rate of no less than 50%, no less than 60%, no less than 70%, no less than 80%, no less than 90%, at a period of 15 minutes in 900 ml of 0.01N HCl with 0.5% sodium lauryl sulphate (SLS), when tested in a USP Type 2 apparatus with sinkers at 50 rpm and 37° C.

In some embodiments, the celecoxib compositions of present application comprises reduced dose of celecoxib, wherein said composition provides similar or higher $AUC_{0-15\ min}$, $AUC_{0-30\ min}$, $AUC_{0-1\ hour}$, and $AUC_{0-2\ hour}$, compared to conventional celecoxib compositions such as CELEBREX® oral capsules.

In some embodiments, the celecoxib compositions of present application comprises reduced dose of celecoxib, wherein said composition provides $AUC_{0-15\ min}$ of at least 50 times higher compared to conventional celecoxib compositions such as CELEBREX® oral capsules.

In some embodiments, the celecoxib compositions of present application comprises reduced dose of celecoxib, wherein said composition provides $AUC_{0-30\ min}$ of at least 12 times higher compared to conventional celecoxib compositions such as CELEBREX® oral capsules.

In some embodiments, the celecoxib compositions of present application comprises reduced dose of celecoxib, wherein said composition provides $AUC_{0-1\ hour}$ of at least 5 times higher compared to conventional celecoxib compositions such as CELEBREX® oral capsules.

In some embodiments, the celecoxib compositions of present application comprises reduced dose of celecoxib, wherein said composition provides $AUC_{0-2\ hour}$ of at least 1.5 times higher compared to conventional celecoxib compositions such as CELEBREX® oral capsules.

In some embodiments, the celecoxib compositions of present application comprises reduced dose of celecoxib, wherein said composition provides similar or higher $AUC_{0-15\ min}$, $AUC_{0-30\ min}$, $AUC_{0-1\ hour}$, and $AUC_{0-2\ hour}$, compared to conventional celecoxib compositions comprising 400 mg of celecoxib such as CELEBREX® 400 mg oral capsules.

In some embodiments, the present application provides an oral liquid pharmaceutical composition comprising therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides at least one of the following pharmacokinetic parameters:
  a) $AUC_{(0-15\ min)}$ from about 10 ng·h/mL to about 80 ng·h/mL;
  b) $AUC_{(0-30\ min)}$ from about 80 ng·h/mL to about 400 ng·h/mL;
  c) $AUC_{(0-1\ hr)}$ from about 400 ng·h/mL to about 1500 ng·h/mL;
  d) $AUC_{(0-2\ hr)}$ from about 1000 ng·h/mL to about 4000 ng·h/mL;
  e) $AUC_{(0-t)}$ of at least about 2000 ng·h/mL;
  f) $AUC_{(0-\infty)}$ of at least about 2000 ng·h/mL; and
  g) $T_{lag}$ of not more than 8 minutes.

In some embodiments, the present application provides an oral liquid pharmaceutical composition comprising therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00 and upon oral administration to a human subject under fasting conditions provides at least one of the following pharmacokinetic parameters:
  a) $AUC_{(0-15\ min)}$ from about 10 ng·h/mL to about 80 ng·h/mL;
  b) $AUC_{(0-30\ min)}$ from about 80 ng·h/mL to about 400 ng·h/mL;
  c) $AUC_{(0-1\ hr)}$ from about 400 ng·h/mL to about 1500 ng·h/mL;
  d) $AUC_{(0-2\ hr)}$ from about 1000 ng·h/mL to about 4000 ng·h/mL;
  e) $AUC_{(0-t)}$ of at least about 2000 ng·h/mL;
  f) $AUC_{(0-\infty)}$ of at least about 2000 ng·h/mL; and
  g) $T_{lag}$ of not more than 8 minutes.

In some embodiments, the celecoxib compositions of present application comprises of therapeutically effective amount of celecoxib, at least one solubiliser, at least one medium chain glyceride and at least one pharmaceutically acceptable excipient; wherein said composition
  a) releases no less than 70% at a period of 10 minutes; or
  b) releases no less than 80% at a period of 15 minutes,
in 900 ml of 0.01N HCl with 0.5% sodium lauryl sulphate (SLS), when tested in a USP Type 2 apparatus with sinkers at 50 rpm and 37° C.

In some embodiments, the celecoxib compositions of present application comprises of therapeutically effective amount of celecoxib, at least one solubiliser, at least one medium chain glyceride, at least one polar solvent and at least one pharmaceutically acceptable excipient; wherein said composition
  a) releases no less than 70% at a period of 10 minutes; or
  b) releases no less than 80% at a period of 15 minutes,
in 900 ml of 0.01N HCl with 0.5% sodium lauryl sulphate (SLS), when tested in a USP Type 2 apparatus with sinkers at 50 rpm and 37° C.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $AUC_{(0-15\ min)}$ at least about 10 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $AUC_{(0-15\ min)}$ from about 10 ng·h/mL to about 80 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $AUC_{(0-30\ min)}$ at least about 80 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $AUC_{(0-30\ min)}$ from about 80 ng·h/mL to about 400 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $AUC_{(0-1\ hr)}$ at least about 400 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $AUC_{(0-1\ hr)}$ from about 400 ng·h/mL to about 1500 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $AUC_{(0-2\ hr)}$ at least about 1000 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $AUC_{(0-2\ hr)}$ from about 1000 ng·h/mL to about 4000 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $AUC_{(0-t)}$ of at least about 2000 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $AUC_{(0-\infty)}$ of at least about 2000 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $T_{lag}$ of not more than 10 minutes.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $T_{lag}$ of not more than 8 minutes.

In some embodiments, the celecoxib composition of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $T_{lag}$ of not more than 5 minutes.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $T_{max}$ of less than about 90 minutes.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition upon oral administration to a human subject under fasting conditions provides $T_{max}$ of less than about 60 minutes.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00; and said composition upon oral administration to a human subject under fasting conditions provides $AUC_{(0-15\ min)}$ at least about 10 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00; and said composition upon oral administration to a human subject under fasting conditions provides $AUC_{(0-15\ min)}$ from about 10 ng·h/mL to about 80 ng·h/mL.

In some embodiments, the celecoxib compositions of celecoxib of the present application comprises of therapeutically effective amount of celecoxib, at least one solubiliser, at least one medium chain glyceride, at least one polar solvent and at least one of pharmaceutically acceptable excipient, wherein said composition comprises solubiliser and polar solvent in the ratio of from about 0.60:1.00 to about 1.8:1.00; and said composition upon oral administration to a human subject under fasting conditions provides $AUC_{(0-30\ min)}$ at least about 80 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00; and said composition upon oral administration to a human subject under fasting conditions provides $AUC_{(0-30\ min)}$ from about 80 ng·h/mL to about 400 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00; and said composition upon oral administration to a human subject under fasting conditions provides $AUC_{(0-1\ hr)}$ at least about 400 ng·h/mL.

In some embodiments the celecoxib compositions of present application comprises of therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00; and said composition upon oral administration to a human subject under fasting conditions provides $AUC_{(0-1\ hr)}$ from about 400 ng·h/mL to about 1500 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00; and said composition upon oral administration to a human subject under fasting conditions provides $AUC_{(0-2\ hr)}$ at least about 1000 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00 and; said composition upon oral administration to a human subject under fasting conditions provides $AUC_{(0-2\ hr)}$ from about 1000 ng·h/mL to about 4000 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00 and upon oral administration to a human subject under fasting conditions provides $AUC_{(0-t)}$ of at least about 2000 ng·h/mL.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00; and said composition upon oral administration to a human subject under fasting conditions provides $AUC_{(0-\infty)}$ of at least about 2000 ng·h/mL In some embodiments, the compositions of celecoxib of the present application comprises of therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00; and said composition upon oral administration to a human subject under fasting conditions provides $T_{lag}$ of not more than 10 minutes.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00; and said composition upon oral administration to a human subject under fasting conditions provides $T_{lag}$ of not more than 8 minutes.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00; and said composition upon oral administration to a human subject under fasting conditions provides $T_{lag}$ of not more than 5 minutes.

In some embodiments, the celecoxib compositions of present application comprises of therapeutically effective amount of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00; and said composition upon oral administration to a human subject under fasting conditions provides $T_{max}$ of less than about 90 minutes.

Improved Physical Properties

In some embodiments, the stable oral liquid pharmaceutical compositions disclosed herein possess improved physical properties, such as droplet size, viscosity, etc. The D50 and D90 represent, the median or the 50$^{th}$ percentile and the 90$^{th}$ percentile of the oil droplet size distribution, respectively, as measured by volume. This means, the term "D50" is defined as the size in nm (nanometers) below which 50 percent of the oil droplets reside on a volume basis and similarly, the term "D90" is defined as the size in nm (nanometers) below which 90% of the oil droplets reside, on a volume basis. Oil droplet size can be determined, for example, by laser light scattering using a particle size analyzer, such as the proprietary Zetasizer™ apparatus available from Malvern Instruments Ltd.

In some embodiments, the celecoxib compositions of present application comprises of therapeutically effective amount of celecoxib, at least one solubiliser, at least one medium chain glyceride and at least one pharmaceutically acceptable excipient, wherein said compositions does not show any precipitation in Fasted-State Simulated Gastric Fluid (FaSSGF) at pH 2.0, temperature of 37° C.±0.5° C. and under stirring at a speed of 50 rpm at least for 60 minutes and said composition has a mean oil droplet size of not more than 500 nm.

A ternary phase diagram is drawn (FIG. 1) which depicts the "stable composition region A". The "stable composition region A" is defined by shaded region or the region between the connecting lines between six points (a, b, c, d, e and f). Any composition that is outside of this region does not form an acceptable composition because either the onset of precipitation time is less than 60 minutes; D50 oil droplet size is more than about 250 nm or D90 oil droplet size is more than about 500 nm.

In one embodiment, stable compositions of celecoxib as per present application that comprises
  a) therapeutically effective amount of celecoxib, at least one solubiliser, at least one medium chain glyceride; and
  b) polar solvent comprising mixture of ethanol and glycerin;
wherein the composition falls within the shaded region of a phase diagram, as shown in FIG. 1, wherein boundaries of a stable composition are defined by shaded region or the region between the connecting lines between the six points (a, b, c, d, e and f), wherein the composition comprises about 1% to about 80% w/w celecoxib and correspond to a weight % ratio of base composition:ethanol:glycerin of 0.200:0.024:0.712 for a, 0.200:0.376:0.360 for b, 0.200:0.400:0.336 for c, 0.536:0.400:0.000 for d, 0.900:0.036:0.00 for e and 0.900:0.00:0.036 for f.

Figure 2:
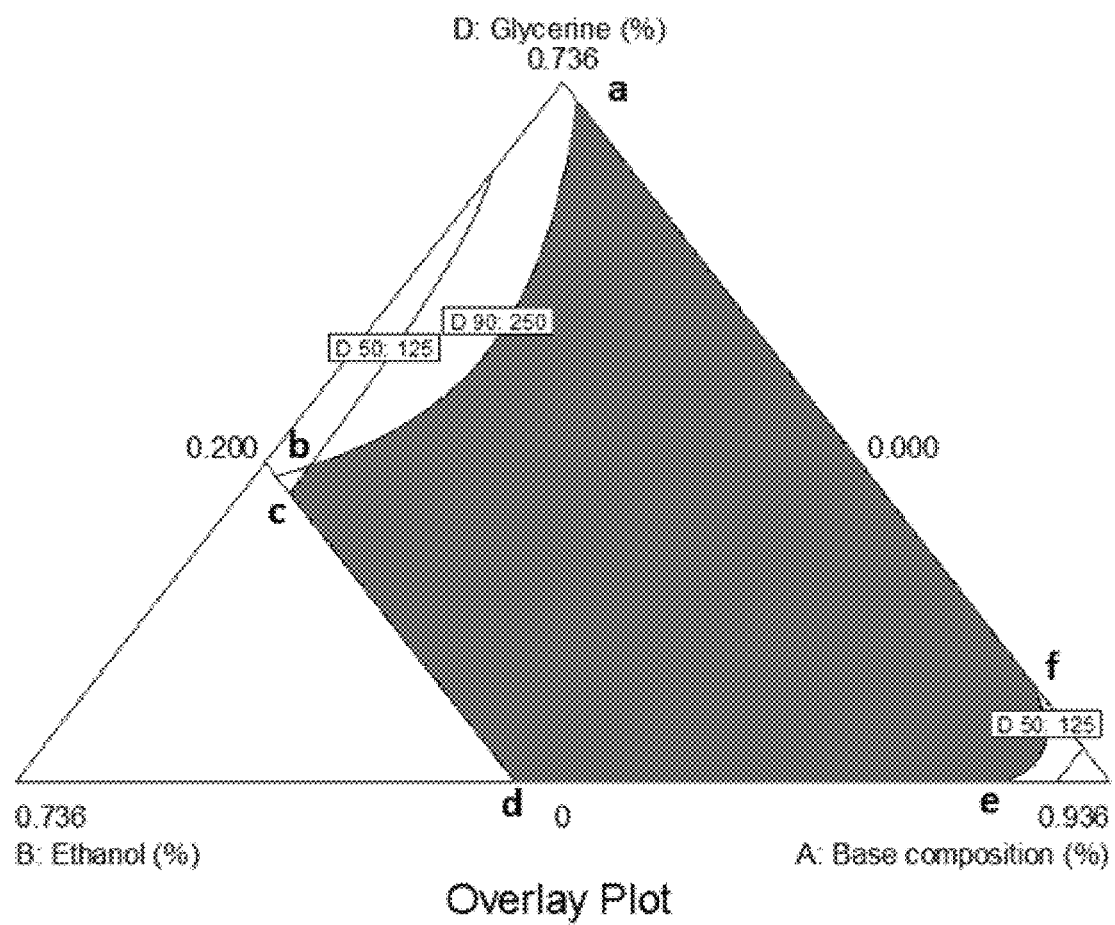
FIG. 2 shows a ternary phase diagram. The shaded region is "stable composition region B" and is formed by connecting lines between points (a, b, c, d, e and f).

A ternary phase diagram is drawn FIG. 2 which depicts the "stable composition region B". The "stable composition region B" is defined by shaded region or the region between the connecting lines between six points (a, b, c, d, e and f). Any composition that is outside of this region does not form an acceptable composition because either the onset of precipitation time is less than 60 minutes; D50 oil droplet size is more than about 125 nm or D90 oil droplet size is more than about 250 nm.

In one embodiment, stable compositions of celecoxib as per present application that comprises
  a) therapeutically effective amount of celecoxib, at least one solubiliser, at least one medium chain glyceride; and
  b) polar solvent comprising mixture of ethanol and glycerin;
wherein the composition falls within shaded region of a phase diagram, as shown in FIG. 2, wherein boundaries of a stable composition are defined by shaded region or the region between the connecting lines between the six points (a, b, c, d, e and f), wherein the composition comprises about 1% to about 80% w/w celecoxib and correspond to a weight % ratio of base composition:ethanol:glycerin of 0.226:0.000:0.710 for a, 0.235:0.371:0.330 for b, 0.236:0.400:0.300 for c, 0.536:0.400:0.000 for d, 0.865:0.071:0.000 for e and 0.836:0.000:0.100 for f.

A ternary phase diagram is drawn (FIG. 3) which depicts the "stable composition region C". The "stable composition region C" is defined by shaded region or the region between the connecting lines between eight points (a, b, c, d, e, f, g and h). Any composition that is outside of this shaded region does not form an acceptable composition because either the onset of precipitation time is less than 60 minutes; D50 oil droplet size is more than about 50 nm or D90 oil droplet size is more than about 100 nm.

Figure 3:
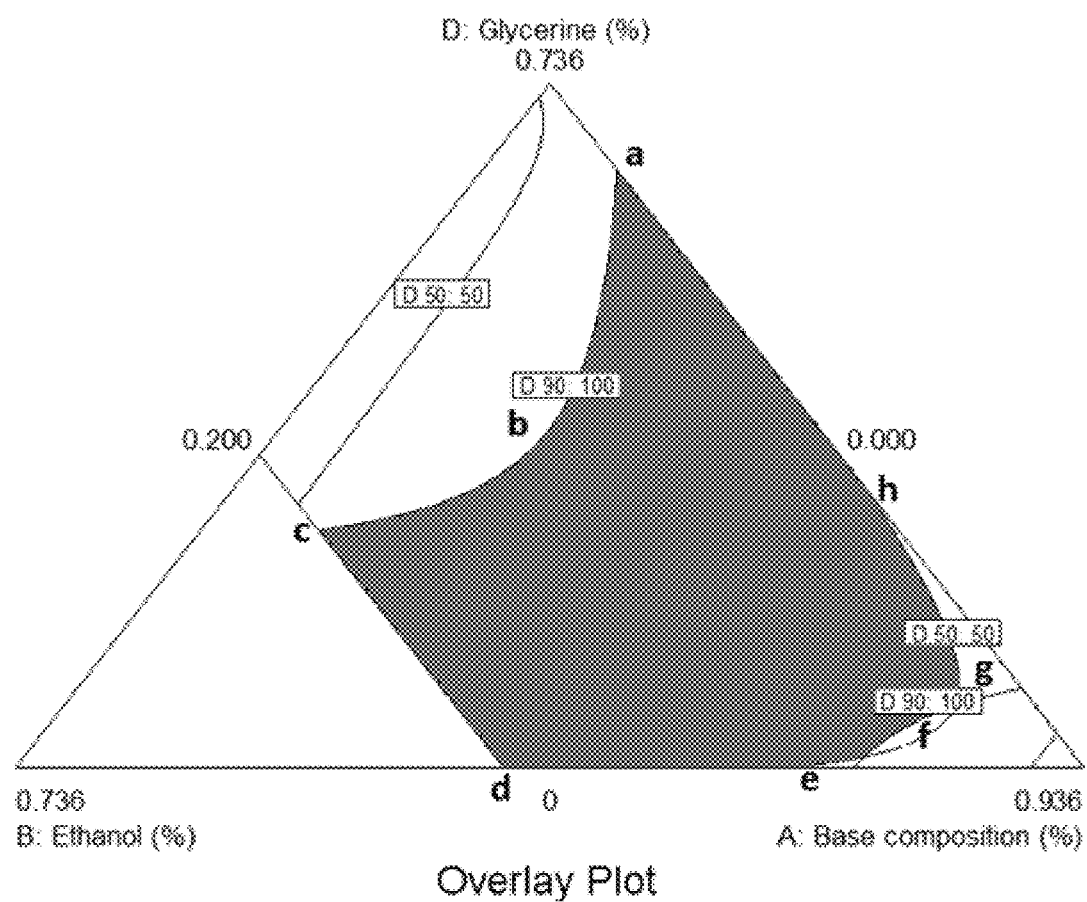
FIG. 3 shows a ternary phase diagram. The shaded region is "stable composition region C" and is formed by connecting lines between points (a, b, c, d, e, f, g and h).

In one embodiment, stable compositions of celecoxib as per present application that comprises
c) therapeutically effective amount of celecoxib, at least one solubiliser, at least one medium chain glyceride; and
d) polar solvent comprising mixture of ethanol and glycerin;
wherein the composition falls within region of a phase diagram, as shown in FIG. 3, wherein boundaries of a stable composition are defined by shaded region or the region between the connecting lines between the eight points (a, b, c, d, e, f, g and h) wherein the composition comprises about 1% to about 80% w/w celecoxib and correspond to a weight % ratio of base composition:ethanol:glycerin is 0.300:0.000: 0.636 for a, 0.385:0.206:0.345 for b, 0.283:0.399:0.254 for c, 0.536:0.400:0.000 ford, 0.745:0.191:0.000 for e, 0.778: 0.144:0.014 for f, 0.817:0.056:0.063 for g and 0.636:0.000: 0.300 for h.

In some embodiments, the stable compositions depicted by "stable composition region A", "stable composition region B" and "stable composition region C" within the region of the phase diagrams, wherein the compositions comprises reduced dose of celecoxib, wherein the reduced dose of celecoxib provides similar or higher $AUC_{0-15\ min}$, $AUC_{0-30\ min}$, $AUC_{0-1\ hour}$ and $AUC_{0-2\ hour}$ compared to conventional celecoxib compositions such as CELEBREX® oral capsules.

In another aspect of above embodiments, the stable compositions depicted by "stable composition region A", "stable composition region B" and "stable composition region C" shown in the shaded region of the phase diagrams, wherein the compositions are essentially free of precipitation inhibitors such as, polyoxyethylene-polyoxypropylene block copolymers, pluronics, polyvinylpyrrolidone, hydroxypropyl cellulose and hydroxypropyl methylcellulose.

In another aspect of above embodiments, the stable compositions depicted by "stable composition region A", "stable composition region B" and "stable composition region C" shown in the shaded region of the phase diagrams, wherein the compositions
a) releases no less than 70% at a period of 10 minutes; or
b) releases no less than 80% at a period of 15 minutes,
in 900 ml of 0.01N HCl with 0.5% sodium lauryl sulphate (SLS), when tested in a USP Type 2 apparatus with sinkers at 50 rpm and 37° C.

In another aspect of above embodiments, the stable compositions depicted by "stable composition region A", "stable composition region B" and "stable composition region C" shown in the shaded region of the phase diagrams, wherein said composition in the form of a solution, suspension, emulsion or liquid mixture.

In another aspect of above embodiments, the stable compositions depicted by "stable composition region A", "stable composition region B" and "stable composition region C" shown in the shaded region of the phase diagrams, wherein said composition has a viscosity of from about 20 cps to about 1000 cps and has a density of from about 0.8 gm/cm3 to about 2 gm/cm3.

In another aspect of above embodiments, the stable compositions depicted by "stable composition region A", "stable composition region B" and "stable composition region C" shown in the shaded region of the phase diagrams, wherein the composition has transmittance of at least 40%.

In another aspect of above embodiments, the stable compositions depicted by "stable composition region A", "stable composition region B" and "stable composition region C" shown in the shaded region of the phase diagrams, wherein the composition has pH of from about 3 to about 7.

In some embodiments, the stable compositions depicted by "stable composition region A", "stable composition region B" and "stable composition region C" shown in the shaded region of the phase diagrams, wherein said composition
c) releases no less than 70% at a period of 10 minutes; or
a) releases no less than 80% at a period of 15 minutes,
in 900 ml of 0.01N HCl with 0.5% sodium lauryl sulphate (SLS), when tested in a USP Type 2 apparatus with sinkers at 50 rpm and 37° C.

In some embodiments, the stable compositions depicted by "stable composition region A", "stable composition region B" and "stable composition region C" shown in the shaded region of a phase diagrams, wherein the composition upon oral administration to a human subject under fasting conditions provides $AUC_{(0-15\ min)}$ at least about 10 ng·h/mL.

In some embodiments, the stable compositions depicted by "stable composition region A", "stable composition region B", and "stable composition region C" shown in the shaded region of a phase diagram, wherein the composition upon oral administration to a human subject under fasting conditions provides $AUC_{(0-15\ min)}$ from about 10 ng·h/mL to about 80 ng·h/mL.

In some embodiments, the stable compositions depicted by "stable composition region A", "stable composition region B" and "stable composition region C" shown in the shaded region of the phase diagram, wherein said composition upon oral administration to a human subject under fasting conditions provides $AUC_{(0-30\ min)}$ at least about 80 ng·h/mL.

In some embodiments, the stable compositions depicted by "stable composition region A", "stable composition region B" and "stable composition region C" shown in the shaded region of the phase diagrams, wherein said composition upon oral administration to a human subject under fasting conditions provides $AUC_{(0-30\ min)}$ from about 80 ng·h/mL to about 400 ng·h/mL.

In some embodiments, the stable compositions depicted by "stable composition region A", "stable composition region B" and "stable composition region C" shown in the shaded region of the phase diagrams, wherein said composition upon oral administration to a human subject under fasting conditions provides $AUC_{(0-1\ hr)}$ at least about 400 ng·h/mL.

In some embodiments, the stable compositions depicted by "stable composition region A", "stable composition region B" and "stable composition region C" shown in the shaded region of a phase diagrams, wherein said composition upon oral administration to a human subject under fasting conditions provides $AUC_{(0-1\ hr)}$ from about 400 ng·h/mL to about 1500 ng·h/mL.

In some embodiments, the stable compositions depicted by "stable composition region A", "stable composition region B" and "stable composition region C" shown in the shaded region of a phase diagrams, wherein said composition upon oral administration to a human subject under fasting conditions provides $AUC_{(0\text{-}2\ hr)}$ at least about 1000 ng·h/mL.

In some embodiments, the stable compositions depicted by "stable composition region A", "stable composition region B" and "stable composition region C" shown in the shaded region of a phase diagrams, wherein said composition upon oral administration to a human subject under fasting conditions provides AUC(0-2 hr) from about 1000 ng·h/mL to about 4000 ng·h/mL.

In some embodiments, the stable compositions depicted by "stable composition region A", "stable composition region B" and "stable composition region C" shown in the shaded region of a phase diagrams, wherein said composition upon oral administration to a human subject under fasting conditions provides AUC(0-t) of at least about 2000 ng·h/mL.

In some embodiments, the stable compositions depicted by "stable composition region A", "stable composition region B" and "stable composition region C" shown in the shaded region of a phase diagrams, wherein said composition upon oral administration to a human subject under fasting conditions provides $AUC_{(0\text{-}t)}$ of at least about 2000 ng·h/mL.

In some embodiments, the stable compositions depicted by "stable composition region A", "stable composition region B" and "stable composition region C" shown in the shaded region of a phase diagrams, wherein said composition upon oral administration to a human subject under fasting conditions provides $T_{lag}$ of not more than 8 minutes.

In some embodiments, the stable compositions depicted by "stable composition region A", "stable composition region B" and "stable composition region C" shown in the shaded region of a phase diagrams, wherein said composition upon oral administration to a human subject under fasting conditions provides $T_{max}$ of less than about 90 minutes.

In some embodiments, the stable compositions depicted by "stable composition region A", "stable composition region B", and "stable composition region C" shown in the shaded region of a phase diagrams, wherein said composition upon oral administration to a human subject under fasting conditions provides at least one of the following pharmacokinetic parameters:

a) $AUC_{(0\text{-}15\ min)}$ from about 10 ng·h/mL to about 80 ng·h/mL;
b) $AUC_{(0\text{-}30\ min)}$ from about 80 ng·h/mL to about 400 ng·h/mL;
c) $AUC_{(0\text{-}1\ hr)}$ from about 400 ng·h/mL to about 1500 ng·h/mL;
d) $AUC_{(0\text{-}2\ hr)}$ from about 1000 ng·h/mL to about 4000 ng·h/mL;
e) $AUC_{(0\text{-}t)}$ of at least about 2000 ng·h/mL;
f) $AUC_{(0\text{-}\infty)}$ of at least about 2000 ng·h/mL; and
g) $T_{lag}$ of not more than 8 minutes.

In some embodiments, the stable compositions depicted by "stable composition region A", "stable composition region B", and "stable composition region C" shown in the shaded region of a phase diagrams, wherein said composition comprising reduced dose of celecoxib upon oral administration to a human subject under fasting conditions provides at least one of the following pharmacokinetic parameters:

a) $AUC_{(0\text{-}15\ min)}$ from about 10 ng·h/mL to about 80 ng·h/mL;
b) $AUC_{(0\text{-}30\ min)}$ from about 80 ng·h/mL to about 400 ng·h/mL;
c) $AUC_{(0\text{-}1\ hr)}$ from about 400 ng·h/mL to about 1500 ng·h/mL;
d) $AUC_{(0\text{-}2\ hr)}$ from about 1000 ng·h/mL to about 4000 ng·h/mL;
e) $AUC_{(0\text{-}t)}$ of at least about 2000 ng·h/mL;
f) $AUC_{(0\text{-}\infty)}$ of at least about 2000 ng·h/mL; and
g) $T_{lag}$ of not more than 8 minutes.

The stable oral liquid pharmaceutical compositions disclosed herein can comprise a variety of mean oil droplet sizes. In some embodiments, the composition provides mean oil droplet size of not more than 500 nm, not more than 250 nm, not more than 100 nm, not more than 50 nm.

In some embodiments, the celecoxib composition of present application is stable and does not show any precipitation in Fasted-State Simulated Gastric Fluid (FaSSGF) at pH 2.0, temperature of 37° C.±0.5° C. and under stirring at a speed of 50 rpm at least for 60 minutes and said composition has a mean oil droplet size of not more than 500 nm.

In some embodiments, the celecoxib composition of present application is stable and does not show any precipitation in Fasted-State Simulated Gastric Fluid (FaSSGF) at pH 2.0, temperature of 37° C.±0.5° C. and under stirring at a speed of 50 rpm at least for 60 minutes and said composition has a mean oil droplet size of not more than 250 nm.

In some embodiments, the celecoxib composition of present application is stable and does not show any precipitation in Fasted-State Simulated Gastric Fluid (FaSSGF) at pH 2.0, temperature of 37° C.±0.5° C. and under stirring at a speed of 50 rpm at least for 60 minutes and said composition has a mean oil droplet size of not more than 100 nm.

In some embodiments, the celecoxib composition of present application is stable and does not show any precipitation in Fasted-State Simulated Gastric Fluid (FaSSGF) at pH 2.0, temperature of 37° C.±0.5° C. and under stirring at a speed of 50 rpm at least for 60 minutes and said composition has a mean oil droplet size of composition is not more than 50 nm.

The stable oral liquid pharmaceutical compositions disclosed herein can comprise a variety of viscosities. In some embodiments, the stable oral liquid composition of celecoxib of the present application has a viscosity that is about 20 cps, about 40 cps, about 60 cps, about 80 cps, about 100 cps, about 200 cps, about 500 cps, about 1000 cps, or a range between any two of the above values.

The stable oral liquid pharmaceutical compositions disclosed herein can comprise a variety of densities. In some embodiments, the stable oral liquid composition of celecoxib of the present application has a density of from about 0.8 gm/cm$^3$ to about 2 gm/cm$^3$.

In some embodiment, the composition provides mean oil droplet size of not more than 500 nm or not more than 250 nm or not more than 100 nm or not more than 50 nm.

In some embodiments, the stable oral liquid composition of the present application has a viscosity of from about 20 cps to about 1000 cps.

In some embodiments, the stable oral liquid composition of the present application has a density of from about 0.8 gm/cm$^3$ to about 2 gm/cm$^3$.

In some embodiments, the stable oral liquid composition of the present application has transmittance of at least 40%.

In some embodiments, the stable oral liquid composition of the present application has a pH of from about 3 to about 7.

In some embodiments, the celecoxib compositions of present application further comprises of water in amount less than about 10%, based on total weight of the composition.

The stable oral liquid pharmaceutical compositions disclosed herein can comprise a variety of transmittances. In some embodiments, the stable oral liquid composition of celecoxib of present application has transmittance of at least 40%. In some embodiments, the stable oral liquid composition of celecoxib of present application has transmittance of more than 40%.

The stable oral liquid pharmaceutical compositions disclosed herein can comprise a variety of pH values. In some embodiments, the stable oral liquid composition of celecoxib of present application has pH of from about 3 to about 7.

In some embodiments, the present application provides an stable oral liquid pharmaceutical composition of celecoxib comprising:
  a. therapeutically effective amount of celecoxib;
  b. at least one solubiliser in amount from about 35% w/w to about 45 w/w;
  c. at least one polar solvent in amount from about 25% w/w to about 42% w/w; and
  d. at least one pharmaceutically acceptable excipient,
wherein said solubiliser and polar solvent are present in the ratio of from about 0.60:1.00 to about 1.8:1.00 and wherein said composition has a viscosity of from about 20 cps to about 1000 cps and density of from about 0.8 gm/cm$^3$ to about 2 gm/cm$^3$.

Improved Stability

In some embodiments, present application relates to a composition comprising therapeutically effective amount of celecoxib, at least one solubiliser, at least one medium chain glyceride and at least one pharmaceutically acceptable excipients, wherein said composition does not show any precipitation in Fasted-State Simulated Gastric Fluid (FaSSGF) at pH 2.0, temperature of 37° C.±0.5° C. and under stirring at a speed of 50 rpm at least for 60 minutes.

In some embodiments, the stable oral liquid composition of celecoxib of the present application is essentially free of precipitation inhibitors such as, polyoxyethylene-polyoxypropylene block copolymers, pluronics, polyvinylpyrrolidone, hydroxypropyl cellulose and hydroxypropyl methylcellulose.

In some embodiments, the present application provides a stable oral pharmaceutical composition comprising therapeutically effective amount of celecoxib, at least one solubiliser, at least one medium chain glyceride and at least one pharmaceutically acceptable excipients, wherein said composition does not show any precipitation in Fasted-State Simulated Gastric Fluid (FaSSGF) at pH of 2.0, temperature of 37° C.±0.5° C. and under stirring at a speed of 50 rpm, when measured at 30 min or 60 min or 90 min or 120 minutes or 180 minutes or 240 minutes time points; and said composition is essentially free of precipitation inhibitors such as, polyoxyethylene-polyoxypropylene block copolymers, pluronics, polyvinylpyrrolidone, hydroxypropyl cellulose and hydroxypropyl methylcellulose.

In some embodiments, the present application provides a stable oral liquid pharmaceutical composition comprising therapeutically effective amount of celecoxib, at least one solubiliser, at least one medium chain glyceride and at least one pharmaceutically acceptable excipients, wherein said composition does not show any precipitation in Fasted-State Simulated Gastric Fluid (FaSSGF) at pH of 2.0, temperature of 37° C.±0.5° C. and under stirring at a speed of 50 rpm, when measured at 30 min or 60 min or 90 min or 120 minutes or 180 minutes or 240 minutes time points; and said composition is essentially free of precipitation inhibitors such as, polyoxyethylene-polyoxypropylene block copolymers, pluronics, polyvinylpyrrolidone, hydroxypropyl cellulose and hydroxypropyl methylcellulose.

In some embodiment, the composition provides mean oil droplet size of not more than 500 nm or not more than 250 nm or not more than 100 nm or not more than 50 nm.

In some embodiments, the stable oral liquid composition of the present application has a viscosity of from about 20 cps to about 1000 cps.

In some embodiments, the stable oral liquid composition of the present application has a density of from about 0.8 gm/cm$^3$ to about 2 gm/cm$^3$.

In some embodiments, the stable oral liquid composition of the present application has transmittance of at least 40%.

In some embodiments, the stable oral liquid composition of the present application has a pH of from about 3 to about 7.

In some embodiments, the present application provides an stable oral liquid pharmaceutical composition of celecoxib comprising:
  a. therapeutically effective amount of celecoxib;
  b. at least one solubiliser in amount from about 35% w/w to about 45% w/w;
  c. at least one polar solvent in amount from about 25% w/w to about 42% w/w; and
  d. at least one pharmaceutically acceptable excipient,
wherein said solubiliser and polar solvent are present in the ratio of from about 0.60:1.00 to about 1.8:1.00 and shows no precipitation in Fasted-State Simulated Gastric Fluid (FaSSGF) at pH 2.0, temperature of 37° C.±0.5° C. and under stirring at a speed of 50 rpm at least for 60 minutes.

In some embodiments, the celecoxib compositions of present application comprises of therapeutically effective amount of celecoxib, at least one solubiliser and at least one medium chain glyceride, wherein said composition shows no precipitation in Fasted-State Simulated Gastric Fluid (FaSSGF) at pH 2.0, temperature of 37° C.±0.5° C. and under stirring at a speed of 50 rpm at least for 60 minutes.

In some embodiments, present application relates to a composition comprising therapeutically effective amount of celecoxib, at least one solubiliser and at least one pharmaceutically acceptable excipients, wherein said composition does not show any precipitation in Fasted-State Simulated Gastric Fluid (FaSSGF) at pH 2.0, temperature of 37° C.±0.5° C. and under stirring at a speed of 50 rpm at least for 60 minutes.

In some embodiments, the present application provides a stable oral pharmaceutical composition comprising therapeutically effective amount of celecoxib, at least one solubiliser and at least one pharmaceutically acceptable excipients, wherein said composition does not show any precipitation in Fasted-State Simulated Gastric Fluid (FaSSGF) at pH 2.0, temperature of 37° C.±0.5° C. and under stirring at a speed of 50 rpm, when measured at 30 min or 60 min or 90 min or 120 minutes or 180 minutes or 240 minutes time points; and said composition is essentially free of precipitation inhibitors such as, polyoxyethylene-polyoxypropylene block copolymers, pluronics, polyvinylpyrrolidone, hydroxypropyl cellulose and hydroxypropyl methylcellulose.

In some embodiments, the present application provides a stable oral liquid pharmaceutical composition comprising therapeutically effective amount of celecoxib, at least one solubiliser and at least one pharmaceutically acceptable excipients, wherein said composition does not show any precipitation in Fasted-State Simulated Gastric Fluid (FaSSGF) at pH of 2.0, temperature of 37° C.±0.5° C. and under stirring at a speed of 50 rpm, when measured at 30 min or 60 min or 90 min or 120 minutes or 180 minutes or 240 minutes time points; and said composition is essentially free of precipitation inhibitors such as, polyoxyethylene-polyoxypropylene block copolymers, pluronics, polyvinylpyrrolidone, hydroxypropyl cellulose and hydroxypropyl methylcellulose.

In some embodiments, the present application provides a pharmaceutical composition comprising therapeutically effective amount of celecoxib, at least one solubiliser, at least one polar solvent and at least one pharmaceutically acceptable excipient, wherein said composition does not show any precipitation in Fasted-State Simulated Gastric Fluid (FaSSGF) at pH 2.0, temperature of 37° C.±0.5° C. and under stirring at a speed of 50 rpm at least for 60 minutes.

In some embodiments, the present application provides a stable oral pharmaceutical composition comprising therapeutically effective amount of celecoxib, at least one solubiliser, at least one medium chain glyceride, at least one polar solvent and at least one pharmaceutically acceptable excipients, wherein said composition does not show any precipitation in Fasted-State Simulated Gastric Fluid (FaSSGF) at pH of 2.0, temperature of 37° C.±0.5° C. and under stirring at a speed of 50 rpm, when measured at 30 min or 60 min or 90 min or 120 minutes or 180 minutes or 240 minutes time points; and said composition is essentially free of precipitation inhibitors such as, polyoxyethylene-polyoxypropylene block copolymers, pluronics, polyvinylpyrrolidone, hydroxypropyl cellulose and hydroxypropyl methylcellulose.

In some embodiments, the present application provides a stable oral liquid pharmaceutical composition comprising therapeutically effective amount of celecoxib, at least one solubiliser, at least one medium chain glyceride, at least one polar solvent and at least one pharmaceutically acceptable excipients, wherein said composition does not show any precipitation in Fasted-State Simulated Gastric Fluid (FaSSGF) at pH of 2.0, temperature of 37° C.±0.5° C. and under stirring at a speed of 50 rpm, when measured at 30 min or 60 min or 90 min or 120 minutes or 180 minutes or 240 minutes time points; and said composition is essentially free of precipitation inhibitors such as, polyoxyethylene-polyoxypropylene block copolymers, pluronics, polyvinylpyrrolidone, hydroxypropyl cellulose and hydroxypropyl methylcellulose.

In some embodiments, the oral liquid composition of present application has a viscosity of from about 20 cps to about 1000 cps.

In some embodiments, the oral liquid composition of present application has a density of from about 0.8 gm/cm3 to about 2 gm/cm3.

In some embodiments, the celecoxib composition of present application do not show any precipitation in Fasted-State Simulated Gastric Fluid (FaSSGF) at pH 2.0, temperature of 37° C.±0.5° C. and under stirring at a speed of 50 rpm at least for 240 minutes.

In some embodiments, the celecoxib composition of present application is essentially free of precipitation inhibitors such as, polyoxyethylene-polyoxypropylene block copolymers, pluronics, polyvinylpyrrolidone, hydroxypropyl cellulose and hydroxypropyl methylcellulose.

In some embodiments, the present application provides a composition comprising therapeutically effective amount of celecoxib, at least one solubiliser, at least one medium chain glyceride, at least one polar solvent and at least one pharmaceutically acceptable excipient; wherein said composition provides mean oil droplet size of no more than 500 nm, when subjected to Fasted-State Simulated Gastric Fluid (FaSSGF) at pH of 2.0, temperature of 37° C.±0.5° C. and under stirring at a speed of 50 rpm, measured at 30 min or 60 min or 90 min or 120 minutes or 180 minutes or 240 minutes time points.

In some embodiments, the celecoxib compositions of present application comprises of therapeutically effective amount of celecoxib, at least one solubiliser, at least one medium chain glyceride, at least one polar solvent and at least one pharmaceutically acceptable excipient, and wherein said composition does not show any precipitation in Fasted-State Simulated Gastric Fluid (FaSSGF) at pH of 2.0, temperature of 37° C.±0.5° C. and under stirring at a speed of 50 rpm at least for 240 minutes.

Reduced Dose

It is observed that the oral liquid celecoxib composition of present application exhibits increased bioavailability ($AUC_{0-15\ min}$, $AUC_{0-30\ min}$, $AUC_{0-1\ hour}$, $AUC_{(0-2\ hour)}$ and require smaller dose as compared to conventional composition of celecoxib such as CELEBREX® oral capsules. Thus, oral compositions with lower dose or reduced dose of celecoxib that can achieve the same or better therapeutic effects as observed with larger doses of conventional celecoxib compositions are desired to minimize the adverse effects of celecoxib.

In some embodiments, the compositions of celecoxib of the present application comprises reduced dose of celecoxib, wherein reduced dose of celecoxib provides the same or better therapeutic effects compared to conventional composition of celecoxib such as CELEBREX® oral capsules.

In some embodiments, the compositions of celecoxib of the present application comprises reduced dose of celecoxib, wherein reduced dose of celecoxib provides similar or higher $AUC_{0-15\ min}$, $AUC_{0-30\ min}$, $AUC_{0-1\ hour}$, and $AUC_{0-2\ hour}$ compared to conventional composition of celecoxib such as CELEBREX® oral.

In some embodiments, the celecoxib compositions of present application comprises of reduced dose of celecoxib, wherein the reduction in dose of celecoxib is at least 20% compared to conventional celecoxib compositions such as CELEBREX® oral capsules.

In some embodiments, the celecoxib compositions of present application comprises of reduced dose of celecoxib, wherein the reduction in dose of celecoxib is at least 30% compared to conventional celecoxib compositions such as CELEBREX® oral capsules.

In some embodiments, the celecoxib compositions of present application comprises of reduced dose of celecoxib, wherein the reduction in dose of celecoxib is at least 40% compared to conventional celecoxib compositions such as CELEBREX® oral capsules.

In some embodiments, the celecoxib compositions of present application comprises of reduced dose of celecoxib, wherein the reduction in dose of celecoxib is at least 50% compared to conventional celecoxib compositions such as CELEBREX® oral capsules.

In some embodiments, the celecoxib compositions of present application comprises of reduced dose of celecoxib, wherein the reduction in dose of celecoxib is at least 60% compared to conventional celecoxib compositions such as CELEBREX® oral capsules.

In some embodiments, the celecoxib compositions of present application comprises of reduced dose of celecoxib, wherein the reduction in dose of celecoxib is at least 70% compared to conventional celecoxib compositions such as CELEBREX® oral capsules.

In some embodiments, the celecoxib compositions of present application comprises of reduced dose of celecoxib, wherein the reduction in dose of celecoxib is at least 80% compared to conventional celecoxib compositions such as CELEBREX® oral capsules.

In some embodiments, the celecoxib compositions of present application comprises of reduced dose of celecoxib, wherein the reduction in dose of celecoxib is at least 40% compared to conventional celecoxib compositions comprising 400 mg of celecoxib such as CELEBREX® 400 mg oral capsules.

In some embodiments, the celecoxib compositions of present application comprises of reduced dose of celecoxib, wherein the reduction in dose of celecoxib is at least 55% compared to conventional celecoxib compositions comprising 400 mg of celecoxib such as CELEBREX® 400 mg oral capsules.

In some embodiments, the celecoxib compositions of present application comprises of reduced dose of celecoxib, wherein the reduction in dose of celecoxib is at least 70% compared to conventional celecoxib compositions comprising 400 mg of celecoxib such as CELEBREX® 400 mg oral capsules.

In some embodiments, the celecoxib compositions of present application comprises reduced dose of celecoxib, wherein said reduced dose is from about 100 mg to 250 mg of celecoxib.

In some embodiments, the celecoxib compositions of present application comprises of reduced dose of celecoxib, wherein said reduced dose is about 240 mg.

In some embodiments, the celecoxib compositions of present application comprises of reduced dose of celecoxib, wherein said reduced dose is about 180 mg.

In some embodiments, the celecoxib compositions of present application comprises of reduced dose of celecoxib, wherein said reduced dose is about 120 mg.

In some embodiments, the celecoxib compositions of present application comprises of reduced dose of celecoxib, wherein the reduction in dose of celecoxib is at least 70% compared to conventional celecoxib compositions comprising 400 mg of celecoxib such as CELEBREX® 400 mg oral capsules.

In some embodiments, the celecoxib compositions of present application comprises reduced dose of celecoxib, wherein said reduced dose is from about 100 mg to 250 mg of celecoxib.

In some embodiments, the stable oral liquid celecoxib composition of present application is essentially free of precipitation inhibitors such as, polyoxyethylene-polyoxypropylene block copolymers, pluronics, polyvinylpyrrolidone, hydroxypropyl cellulose and hydroxypropyl methylcellulose.

In some embodiments, the present application provides an oral liquid pharmaceutical composition comprises reduced dose of celecoxib, where in the said reduced dose comprises of from about 100 mg to 250 mg of celecoxib, at least one solubiliser, at least one medium chain glyceride, at least one polar solvent and at least one pharmaceutically acceptable excipient, wherein said composition upon oral administration to a human subject under fasting conditions provides at least one of the following pharmacokinetic parameters:
a) $AUC_{(0\text{-}15\ min)}$ from about 10 ng·h/mL to about 80 ng·h/mL;
b) $AUC_{(0\text{-}30\ min)}$ from about 80 ng·h/mL to about 400 ng·h/mL;
c) $AUC_{(0\text{-}1\ hr)}$ from about 400 ng·h/mL to about 1500 ng·h/mL;
d) $AUC_{(0\text{-}2\ hr)}$ from about 1000 ng·h/mL to about 4000 ng·h/mL;
e) $AUC_{(0\text{-}t)}$ of at least about 2000 ng·h/mL;
f) $AUC_{(0\text{-}\infty)}$ of at least about 2000 ng·h/mL; and
g) $T_{lag}$ of not more than 8 minutes.

In some embodiments, the present application provides an oral liquid pharmaceutical composition comprise reduced dose of celecoxib, where in the said low dose comprises of from about 100 mg to 250 mg of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00 and upon oral administration to a human subject under fasting conditions provides at least one of the following pharmacokinetic parameters:
a) $AUC_{(0\text{-}15\ min)}$ from about 10 ng·h/mL to about 80 ng·h/mL;
b) $AUC_{(0\text{-}30\ min)}$ from about 80 ng·h/mL to about 400 ng·h/mL;
c) $AUC_{(0\text{-}1\ hr)}$ from about 400 ng·h/mL to about 1500 ng·h/mL;
d) $AUC_{(0\text{-}2\ hr)}$ from about 1000 ng·h/mL to about 4000 ng·h/mL;
e) $AUC_{(0\text{-}t)}$ of at least about 2000 ng·h/mL;
f) $AUC_{(0\text{-}\infty)}$ of at least about 2000 ng·h/mL; and
g) $T_{lag}$ of not more than 8 minutes.

In some embodiments, the present application provides an oral liquid pharmaceutical composition of celecoxib, wherein said composition comprises of from about 100 mg to 250 mg of celecoxib, at least one solubiliser, at least one medium chain glyceride, at least one polar solvent and at least one pharmaceutically acceptable excipient, wherein said composition comprises solubiliser and polar solvent in the ratio of from about 0.60:1.00 to about 1.8:1.00 and upon oral administration to a human subject under fasting conditions provides at least one of the following pharmacokinetic parameters:
a) $AUC_{(0\text{-}15\ min)}$ from about 10 ng·h/mL to about 80 ng·h/mL;
b) $AUC_{(0\text{-}30\ min)}$ from about 80 ng·h/mL to about 400 ng·h/mL;
c) $AUC_{(0\text{-}1\ hr)}$ from about 400 ng·h/mL to about 1500 ng·h/mL;
d) $AUC_{(0\text{-}2\ hr)}$ from about 1000 ng·h/mL to about 4000 ng·h/mL;
e) $AUC_{(0\text{-}t)}$ of at least about 2000 ng·h/mL;
f) $AUC_{(0\text{-}\infty)}$ of at least about 2000 ng·h/mL; and
g) $T_{lag}$ of not more than 8 minutes.

Pharmaceutically Acceptable Excipients, Flavoring and Sweetening Agents

In some embodiments, the celecoxib compositions of present application may further contain at least one flavoring agents or taste masking agents. These flavoring agents or taste masking agents are well known in art or approved by US FDA.

Non-limiting exemplary list of flavoring agents/taste masking agents: natural and synthetic flavoring liquids such as volatile oils, synthetic flavor oils, flavoring aromatic and oils, liquids, oleoresins or extracts derived from plants, leaves, flowers, fruits, stems and combinations thereof. Non-limiting representative examples of volatile oils include spearmint oil, cinnamon oil, oil of wintergreen (methyl salicylate), peppermint oil, menthol, clove oil, bay oil, anise oil, eucalyptus oil, thyme oil, cedar leaf oil, oil of nutmeg, allspice oil, oil of sage, mace extract, oil of bitter almond, and cassia oil. Also artificial, natural or synthetic flavors including fruit flavors such as vanilla, and citrus oils including lemon, orange, grape, lime and grapefruit and fruit essences including apple, pear, peach, grape, strawberry, raspberry, cherry, plum, pineapple, apricot, banana and other useful flavorings include aldehydes and esters such as benzaldehyde (cherry, almond), citral, i.e., alphocitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), and 2-dodecenal (citrus, mandarin), bubble gum flavor, mixtures thereof and the like.

Non-limiting exemplary list of sweeteners: sugars such as sucrose, glucose (corn syrup), dextrose, invert sugar, fructose, and mixtures thereof, saccharin and its various salts such as the sodium or calcium salt; cyclamic acid and its various salts such as the sodium salt; the dipeptide sweeteners such as aspartame, acesulfame K, and other sweeteners like magnasweet, sucralose, mixtures thereof and the like.

Methods of Treating Pain

In some embodiments, the present application relates to a method of treating pain in a human subject by orally administering a stable oral liquid pharmaceutical composition as disclosed herein, In some embodiments, the composition comprises a therapeutically effective amount of celecoxib, at least one solubiliser, at least one medium chain glyceride and at least one pharmaceutically acceptable excipients, wherein said composition shows no precipitation in Fasted-State Simulated Gastric Fluid (FaSSGF) at pH 2.0, temperature of 37° C.±0.5° C. and under stirring at a speed of 50 rpm at least for 60 minutes.

In some embodiments, the present application relates to a method of treating pain in a human subject by orally administering a composition comprising therapeutically effective amount of celecoxib, at least one solubiliser, at least one polar solvent, at least one medium chain glyceride and at least one pharmaceutically acceptable excipients, wherein said composition shows no precipitation in Fasted-State Simulated Gastric Fluid (FaSSGF) at pH 2.0, temperature of 37° C.±0.5° C. and under stirring at a speed of 50 rpm at least for 60 minutes.

In some embodiment, the composition provides mean oil droplet size of no more than 1000 nm or not more than 500 nm or not more than 250 nm or not more than 100 nm or not more than 50 nm.

In some embodiments, the present application relates to a method for treating pain in a human subject by orally administering a composition comprising therapeutically effective amount of celecoxib, at least one solubiliser, at least one medium chain glyceride at least one polar solvent and at least one pharmaceutically acceptable excipients, wherein said composition comprises of said solubiliser and polar solvent in the ratio of from about 0.60:1.00 to about 1.8:1.00.

In some embodiments, the present application relates to a method for treating pain in a human subject by orally administering a composition comprising therapeutically effective amount of celecoxib, at least one solubiliser, at least one medium chain glyceride, at least one polar solvent and at least one pharmaceutically acceptable excipients, wherein said composition is essentially free of precipitation inhibitors such as, polyoxyethylene-polyoxypropylene block copolymers, pluronics, polyvinylpyrrolidone, hydroxypropyl cellulose and hydroxypropyl methylcellulose.

In some embodiments, the present application relates to a method for treating pain in a human subject by orally administering a composition comprising therapeutically effective amount of celecoxib, wherein the composition has transmittance of at least 40%.

In some embodiments, the present application relates to a method for treating pain in a human subject by orally administering a composition comprising therapeutically effective amount of celecoxib, wherein the composition has pH of from about 3 to about 7.

In some embodiments, the present application relates to a method for treating pain in a human subject by administering an oral liquid pharmaceutical composition of celecoxib comprising:
a) therapeutically effective amount of celecoxib;
b) at least one solubiliser in an amount from about 35 w/w to about 45 w/w; and
c) at least one polar solvent in an amount from about 25% w/w to about 42% w/w;
d) at least one pharmaceutically acceptable excipients;
wherein said solubiliser and polar solvent are present in the ratio of from about 0.60:1.00 to about 1.8:1.00 and wherein said composition has a viscosity of from about 20 cps to about 1000 cps and density of from about 0.8 gm/cm$^3$ to about 2 gm/cm$^3$.

In some embodiments, the present application relates to a method for treating pain in a human subject by administering an oral liquid pharmaceutical composition of celecoxib comprising:
a) reduced dose of celecoxib, wherein the reduction in dose of celecoxib is at least 20 percent compared to conventional celecoxib compositions;
b) at least one solubiliser in an amount from about 35% w/w to about 45% w/w; and
c) at least one polar solvent in an amount from about 25% w/w to about 42% w/w;
d) at least one pharmaceutically acceptable excipients;
wherein said solubiliser and polar solvent are present in the ratio of from about 0.60:1.00 to about 1.8:1.00 and wherein said composition has a viscosity of from about 20 cps to about 1000 cps and density of from about 0.8 gm/cm$^3$ to about 2 gm/cm$^3$.

In some embodiments, the present application relates to a method for treating pain in a human subject by administering an oral liquid pharmaceutical composition of celecoxib, wherein said composition provides at least one of the following pharmacokinetic parameters upon oral administration to a human subject under fasting conditions:
a) $AUC_{(0-15\ min)}$ from about 10 ng·h/mL to about 80 ng·h/mL;
b) $AUC_{(0-30\ min)}$ from about 80 ng·h/mL to about 400 ng·h/mL;
c) $AUC_{(0-1\ hr)}$ from about 400 ng·h/mL to about 1500 ng·h/mL;
d) $AUC_{(0-2\ hr)}$ from about 1000 ng·h/mL to about 4000 ng·h/mL;
e) $AUC_{(0-t)}$ of at least about 2000 ng·h/mL;
f) $AUC_{(0-\infty)}$ of at least about 2000 ng·h/mL; and
g) $T_{lag}$ of not more than 8 minutes.

In some embodiments, the present application relates to a method for treating pain in a human subject by orally administering a composition comprising therapeutically effective amount of celecoxib, wherein the composition has transmittance of at least 40%.

In some embodiments, the present application relates to a method for treating pain in a human subject by orally administering a composition comprising therapeutically effective amount of celecoxib, wherein the composition has pH of from about 3 to about 7.

In some embodiments, the composition of present application is used for the treatment or ameliorating of pain including, but not limited to, acute pain, migraine pain, cluster headache, neuropathic pain, post-operative pain, chronic lower back pain, herpes neuralgia, phantom limb pain, central pain, dental pain, neuropathic pain, opioid-resistant pain, visceral pain, surgical pain, bone injury pain, arthritis pain, inflammation, osteoarthritis, juvenile rheumatoid arthritis, ankylosing spondylitis, primary dysmenorrhea, pain during labor and delivery, pain resulting from burns, including sunburn, post-partum pain, angina pain, and genitourinary tract-related pain including cystitis, the term shall also refer to nociceptive pain or nociception in patients need thereof.

Methods of Treating Migraine Pain

In some embodiments, the present application relates to a method of treating migraine pain in a human subject by orally administering a stable oral liquid pharmaceutical composition as disclosed herein, In some embodiments, the methods lead to pain free at 2 hours in at least 25%, at least 26%, at least 27%, at least 28%, at least 29%, at least 30%, at least 31%, at least 32%, at least 33%, at least 34%, at least 35%, or more, of the human subjects being treated. In some embodiments, the methods lead to an increase in the percentage of human subjects being treated being pain free at 2 hours that is at least 40%, at least 45%, at least 50%, at least 55%, at least 60%, at least 65%, at least 70%, at least 75%, at least 80%, at least 85%, at least 90%, at least 95%, or more, in comparison to the percentage of human subjects being treated with a placebo. In some embodiments, the methods lead to partial pain relief at 2 hours in at least 45%, at least 50%, at least 60%, at least 65%, at least 66%, at least 67%, at least 68%, at least 69%, at least 70%, at least 71%, at least 72%, at least 73%, at least 74%, at least 75%, or more, of the human subjects being treated. In some embodiments, the methods lead to an increase in the percentage of human subjects being treated being partially relieved of pain at 2 hours that is at least 10%, at least 15%, at least 20%, at least 25%, at least 30%, at least 35%, at least 40%, at least 45%, at least 50%, at least 55%, at least 60%, at least 65%, at least 70%, or more, in comparison to the percentage of human subjects being treated with a placebo.

In some embodiments, the present application relates to a method of treating migraine pain in a human subject by orally administering a composition of Example 3 having 120 mg Celecoxib (Treatment-1). In some embodiments, the methods lead to pain free at 2 hours in at least 25%, at least 26%, at least 27%, at least 28%, at least 29%, at least 30%, at least 31%, at least 32%, at least 33%, at least 34%, at least 35%, or more, of the human subjects being treated. In some embodiments, the methods lead to an increase in the percentage of human subjects being treated being pain free at 2 hours that is at least 40%, at least 45%, at least 50%, at least 55%, at least 60%, at least 65%, at least 70%, at least 75%, at least 80%, at least 85%, at least 90%, at least 95%, or more, in comparison to the percentage of human subjects being treated with a placebo. In some embodiments, the methods lead to partial pain relief at 2 hours in at least 45%, at least 50%, at least 60%, at least 65%, at least 66%, at least 67%, at least 68%, at least 69%, at least 70%, at least 71%, at least 72%, at least 73%, at least 74%, at least 75%, or more, of the human subjects being treated. In some embodiments, the methods lead to an increase in the percentage of human subjects being treated being partially relieved of pain at 2 hours that is at least 10%, at least 15%, at least 20%, at least 25%, at least 30%, at least 35%, at least 40%, at least 45%, at least 50%, at least 55%, at least 60%, at least 65%, at least 70%, or more, in comparison to the percentage of human subjects being treated with a placebo.

In some embodiments, the present application relates to methods, comprising administering a composition of Example 3 having 120 mg Celecoxib (Treatment-1), lead to pain free at 2 hours in at least 26%, at least 27%, at least 28% or at least 29% or at least 30% of the human subjects being treated.

In some embodiments, the present application relates to methods, comprising administering a composition of Example 3 having 120 mg Celecoxib (Treatment-1), lead to partial pain relief at 2 hours in at least at least 63% of the human subjects being treated.

In some embodiments, the methods of using a stable oral liquid pharmaceutical composition as disclosed herein, lead to an increase in the percentage of human subjects being treated being pain free at 2 hours that is at least 10%, at least 15%, at least 20%, at least 25%, at least 30%, at least 35%, at least 40%, at least 45%, at least 50%, at least 55%, at least 60%, at least 65%, at least 70%, or more, in comparison to the percentage of human subjects being treated with a commercially available migraine pain treatment, such as VIOXX 25 (25 mg), VIOXX 50 (50 mg) and CAMBIA 50 (50 mg). In some embodiments, the methods lead to an increase in the percentage of human subjects being treated being partially relieved of pain at 2 hours that is at least 10%, at least 15%, at least 20%, at least 25%, at least 30%, at least 35%, at least 40%, at least 45%, at least 50%, at least 55%, at least 60%, at least 65%, at least 70%, or more, in comparison to the percentage of human subjects being treated with a commercially available migraine pain treatment, such as VIOXX 25 (25 mg), VIOXX 50 (50 mg) and CAMBIA 50 (50 mg). In some embodiments, the methods lead to an increase in the percentage of human subjects being treated being pain free at 2 hours that is at least 10%, at least 15%, at least 20%, at least 25%, at least 30%, at least 35%, at least 40%, at least 45%, at least 50%, at least 55%, at least 60%, at least 65%, at least 70%, or more, in comparison to the percentage of human subjects being treated with a commercially available migraine pain treatment, such as VIOXX 25 (25 mg), VIOXX 50 (50 mg) and CAMBIA 50 (50 mg).

In some embodiments, the methods, comprising administering a composition of Example 3 having 120 mg Celecoxib (Treatment-1), lead to an increase in the percentage of human subjects being treated being pain free at 2 hours that is at least 10%, at least 15%, at least 20%, at least 25%, at least 30%, at least 35%, at least 40%, at least 45%, at least 50%, at least 55%, at least 60%, at least 65%, at least 70%, or more, in comparison to the percentage of human subjects being treated with a commercially available migraine pain treatment, such as VIOXX 25 (25 mg), VIOXX 50 (50 mg) and CAMBIA 50 (50 mg).

In some embodiments, the oral liquid compositions of the present application can be dispensed in liquid form packaged in bottles or any other suitable containers for oral administration. The liquid composition can be ingested with or without further mixing with aqueous or suitable media before oral administration.

In some embodiments, the oral liquid compositions of the present application can be dispensed in container such as a sachet, ampoule, syringe or dropper device or tube or bottle, (for example, a tube or bottle which can be squeezed to deliver its contents), optionally as a fixed dosage, the contents of which may be directly orally ingested or mixed or dispersed into food or liquid.

In some embodiments, the compositions of present application can be formulated as capsule that is suitable for oral administration. The composition can be filled in hard or soft gelatin capsule or HPMC capsules or capsules made up of any other pharmaceutically acceptable materials.

In some embodiments, the composition of present application can be sprayed on inert substrate which can be a powder or a multiparticulate such as a granule, a pellet, a bead, a spherule, a beadlet, a microcapsule, a millisphere, a nanocapsule, a nanosphere or a microsphere.

A substrate constitutes a finely divided (milled, micronized, nanosized, precipitated) form of an inert additive molecular aggregates or a compound aggregate of multiple components or a physical mixture of aggregates of additives. Such substrates can be formed of various materials known in the art, such as, for example: sugars, such as lactose, sucrose or dextrose; polysaccharides, such as maltodextrin or dextrates; starches; cellulosics, such as microcrystalline cellulose or microcrystalline cellulose/sodium carboxymethyl cellulose; inorganics, such as dicalcium phosphate, hydroxyapitite, tricalcium phosphate, talc, or titania; and polyols, such as mannitol, xylitol, sorbitol or cyclodextrin.

EXAMPLES

The following examples are offered to illustrate but not to limit the invention.

Although the invention has been illustrated by the following examples, it is not to be construed as being limited thereby; but rather, the invention encompasses the generic area as hereinbefore disclosed. Various modifications and embodiments can be made without departing from the spirit and scope thereof.

Examples 1-3: Stable Oral Compositions of Celecoxib Used in the Studies

The compositions comprising celecoxib were prepared as given in Table 1.

TABLE 1

Stable oral liquid pharmaceutical compositions used in the studies.

| Ingredients | Example 1 (% w/w) | Example 2 (% w/w) | Example 3 (% w/w) |
| --- | --- | --- | --- |
| Celecoxib | 5.00 | 5.00 | 4.76 |
| Lauroyl macrogolglycerides | 4.17 | 10.00 | 9.52 |
| Glyceryl Monocaprylate | 5.00 | 5.00 | 4.76 |
| Glyceryl Tricaprylate/Tricaprate | 12.50 | 12.50 | 11.90 |
| Polyoxy 35 castor oil | 25.00 | 29.50 | 28.09 |
| PEG-40 Hydrogenated Castor Oil | 10.33 | 0.00 | 0.00 |
| Sweeteners | 8.65 | 8.65 | 1.47 |
| Propyl gallate | 0.02 | 0.02 | 0.00 |
| Menthol | 0.31 | 0.31 | 0.18 |
| flavors | 1.46 | 1.46 | 0.32 |
| Ethanol | 20.00 | 20.00 | 0.00 |
| Glycerine | 5.21 | 5.21 | 0.00 |
| Propylene glycol | 0.00 | 0.00 | 33.87 |
| Purified water | q.s to 100 | q.s to 100 | q.s to 100 |

Manufacturing Procedure:

Celecoxib was added to solubilisers (lauroyl macrogolglycerides, polyoxy 35 castor oil and PEG-40 Hydrogenated Castor Oil) and mixed properly to obtain uniform mixture.

Further to mixture of step 1 medium chain glycerides (caprylic/capric triglyceride and glyceryl caprylate) were added.

To the mixture of step 2, other ingredients such as flavours and sweeteners were added and mixed well.

To the composition of step 3, propylene glycol was added and mixed thoroughly with slight heating 30° C.±5° C. until a uniform dispersion is obtained and cool the solution to 25-30° C. under stirring.

To the composition of step 4, purified water was added and mixed well until a clear solution obtained.

The composition of step 5 was filled in amber colored glass bottle with 18 mm child resistant-tamper evident cap.

Example 4: Evaluation of Onset of Precipitation of the Stable Oral Composition Compositions of Examples 1, 2 & 3 were evaluated for onset of precipitation time.

2 ml of compositions comprising 100 mg of celecoxib were dropped in 250 mL of FaSSGF, pH 2.0, at 37° C. under stirring and onset of precipitation was noted.

TABLE 2

Time for onset of precipitation.

| Composition | Time for onset of precipitation (minutes) | | | | |
| --- | --- | --- | --- | --- | --- |
| | 30 | 60 | 120 | 180 | 240 |
| Example 1 | Precipitation not observed | Precipitation not observed | Precipitation not observed | Precipitation not observed | Precipitation not observed |
| Example 2 | Precipitation not observed | Precipitation not observed | Precipitation not observed | Precipitation not observed | Precipitation not observed |
| Example 3 | Precipitation not observed | Precipitation not observed | Precipitation not observed | Precipitation not observed | Precipitation not observed |

Example 5: Evaluation of Dissolution Release Profile of the Stable Oral Compositions Celecoxib dissolution study of 2 ml of the compositions of Examples 1, 2 & 3 comprising 100 mg of celecoxib was performed in a standard USP dissolution medium under the following conditions: USP apparatus II paddles; dissolution medium (900 ml 0.01N HCl containing 0.5% sodium lauryl sulfate) at a speed of 50 rpm and a temperature of 37° C.

TABLE 3

Dissolution of the stable oral composition in standard USP dissolution medium.

| Sr. No | Time (mins) | Example 1 | Example 2 % Released | Example 3 |
|---|---|---|---|---|
| 1 | 10 | >70 | >70 | >70 |
| 2 | 15 | >80 | >80 | >80 |

Example 6: Evaluation of Physical Properties of Stable Oral Compositions

The composition of Example 3 was found to be stable after subjecting it to stability evaluation conditions of 25° C./60% RH and 40° C./75% RH. The composition was also evaluated for viscosity, density, pH, oil droplet size.

TABLE 4

Physical evaluation of the stable oral composition.

| | Amber color glass bottle with cap | | | | |
|---|---|---|---|---|---|
| Storage container | | 40° C./75% RH | | | 25° C./ 60% RH |
| Parameter | Initial | 1 Month | 2 Month | 3 Month | 3 Month |
| Assay | 101.2 | 99.4 | 100 | 102.6 | 103.3 |
| pH | 5.93 | 5.92 | 5.85 | 5.58 | 5.77 |
| Sing high unknown | 0.03 | 0.02 | 0.02 | 0.01 | 0.02 |
| Total impurity | 0.05 | 0.02 | 0.02 | 0.01 | 0.02 |
| Density (g/ml) | 1.01 | 1.01 | 1.01 | 1.011 | 1.017 |

TABLE 4-continued

Physical evaluation of the stable oral composition.

| | Amber color glass bottle with cap | | | | |
|---|---|---|---|---|---|
| Storage container | | 40° C./75% RH | | | 25° C./ 60% RH |
| Parameter | Initial | 1 Month | 2 Month | 3 Month | 3 Month |
| Viscosity (cps) | 129 | 108.9 | 104.6 | 101.6 | 127.7 |
| D50 oil droplet size | 18.4 | 18.1 | 18.7 | 18.4 | 18.1 |
| D90 oil droplet size | 27.5 | 26.6 | 27.6 | 27.6 | 26.7 |

Example 7: Bioavailability of the Stable Oral Composition

A four-way, randomized, crossover study to compare the bioavailability of Example 3 (Celecoxib Oral Solution) at doses of 120 mg, 180 mg and 240 mg versus CELEBREX® (celecoxib) 400 mg capsules and to determine dose-proportionality of Example 3 formulations in healthy volunteers under fasting conditions.

In each study period, a single dose of celecoxib composition was administered orally, in the morning, following a 10-hour overnight fast. The administration is done as follows:

Treatment-1: Composition of Example 3 containing 120 mg of Celecoxib, administered orally to the volunteers followed by about 240 ml of water.

Treatment-2: Composition of Example 3 containing 180 mg of Celecoxib, administered orally to the volunteers followed by about 240 ml of water.

Treatment-3: Composition of Example 3 containing 240 mg of Celecoxib, administered orally to the volunteers followed by about 240 ml of water.

Treatment-4: An oral 400 mg dose (1×400 mg) CELEBREX® capsule was administered with about 240 mL of water.

Results:

Celecoxib plasma concentrations and other pharmacokinetic parameters were determined. Observed pharmacokinetic parameters are given in Table 5.

TABLE 5

Pharmacokinetic parameters after administration of the stable oral composition.

| Parameters | Treatment-1 (Test 120 mg) Mean ± SD | Treatment-2 (Test 180 mg) Mean ± SD | Treatment-3 (Test 240 mg) Mean ± SD | Treatment-4 (Reference 400 mg) Mean ± SD |
|---|---|---|---|---|
| T lag$^a$ | 4.8 mins (0.0-7.2) | 4.8 mins (0.0-7.2) | 3.0 mins (0.0-7.2) | 10.2 mins (4.8-19.8) |
| $T_{max}^a$ (hrs) | 0.67 (0.50-1.67) | 0.67 (0.50-1.03) | 0.95 (0.50-2.00) | 2.50 (1.67-5.00) |
| $C_{max}$ (ng/mL) | 1061.909 ± 237.632 | 1544.886 ± 289.851 | 1932.543 ± 305.703 | 611.382 ± 222.223 |
| $AUC_{0\_15min}$ (ng · h/mL) | 19.171 ± 10.697 | 26.616 ± 11.819 | 35.155 ± 17.795 | 0.300 ± 0.274 |
| $AUC_{0\_30min}$ (ng · h/mL) | 149.120 ± 50.983 | 227.989 ± 68.623 | 283.211 ± 80.932 | 9.491 ± 5.773 |
| $AUC_{0\_1hour}$ (ng*h/mL) | 604.826 ± 165.795 | 929.510 ± 193.524 | 1151.831 ± 214.121 | 103.166 ± 61.783 |
| $AUC_{0\_2hours}$ (ng*h/mL) | 1322.703 ± 248.613 | 1976.926 ± 382.453 | 2621.176 ± 378.846 | 512.474 ± 292.137 |
| $AUC_{0-t}$ (ng · h/mL) | 3059.684 ± 985.206 | 4633.125 ± 1478.184 | 6621.564 ± 1840.041 | 7288.003 ± 2505.792 |
| $AUC_{0-\infty}$ (ng · h/mL) | 3476.866 ± 1176.823 | 5234.806 ± 1423.726 | 6826.990 ± 1857.487 | 8074.908 ± 2159.266 |

$^a$Median (range)

Example 8: Study on Treatment of Migraine Using the Stable Oral Composition

A three-way, double blind, randomized, crossover study was designed to compare the bioavailability of Example 3 (Celecoxib Oral Solution) at doses of 120 mg and 240 mg versus placebo and to determine efficacy of the stable oral composition in Example 3 in treating migraine. 60 subjects with history of 2-6 episodic migraine were recruited into the study in 6 sites.

In each study period, a single dose of the stable oral composition was administered orally, in the morning, following a 10-hour overnight fast. The administration is done as follows:

Treatment-1: Composition of Example 3 containing 120 mg of Celecoxib, administered orally to the volunteers followed by about 240 ml of water.

Treatment-2: Composition of Example 3 containing 240 mg of Celecoxib, administered orally to the volunteers followed by about 240 ml of water.

Treatment-3: Placebo administered orally to the subjects, followed by about 240 ml of water.

PK samples were collected at home (if feasible for subjects who consented) at 0.5 hr and 2 hr post dosing during actual migraine attack.

Figure 4:
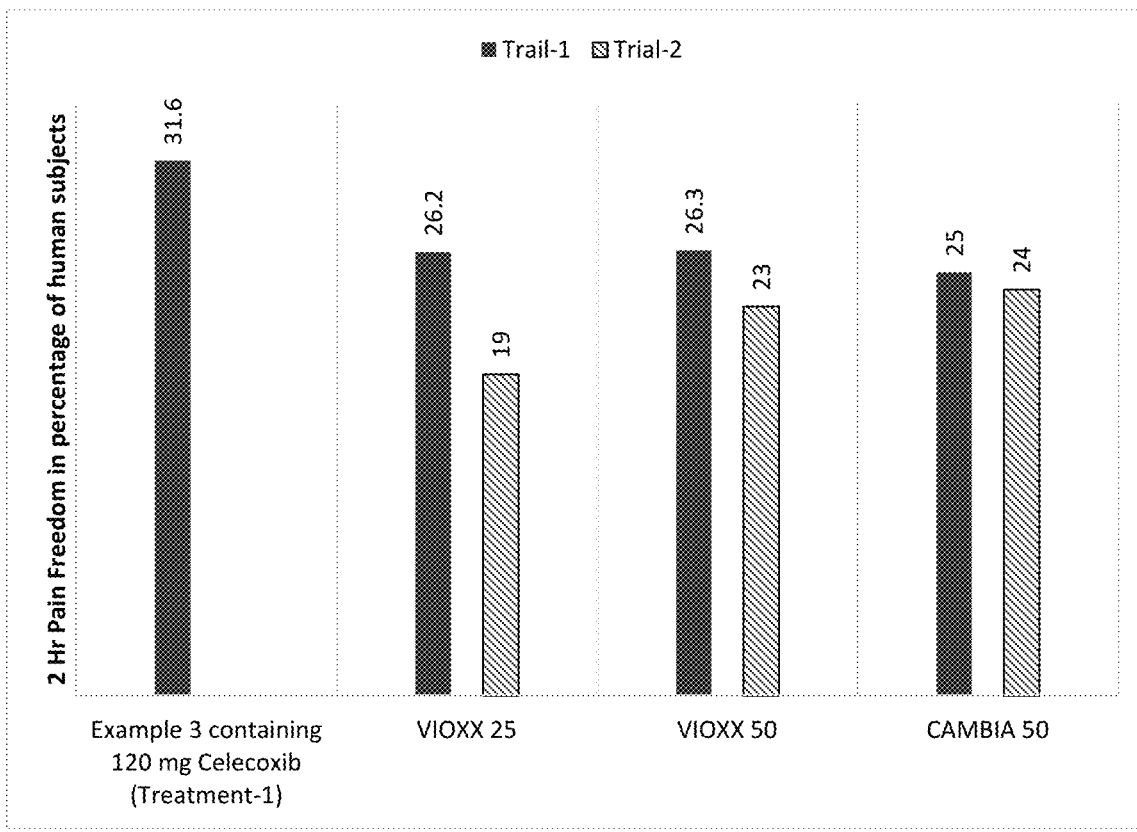
FIG. 4 shows pain free in percentage of human subjects at 2 hours results of the Example 3 having 120 mg Celecoxib (Treatment-1) compared to VIOXX 25, VIOXX 50 & CAMBIA 50.
Figure 5:
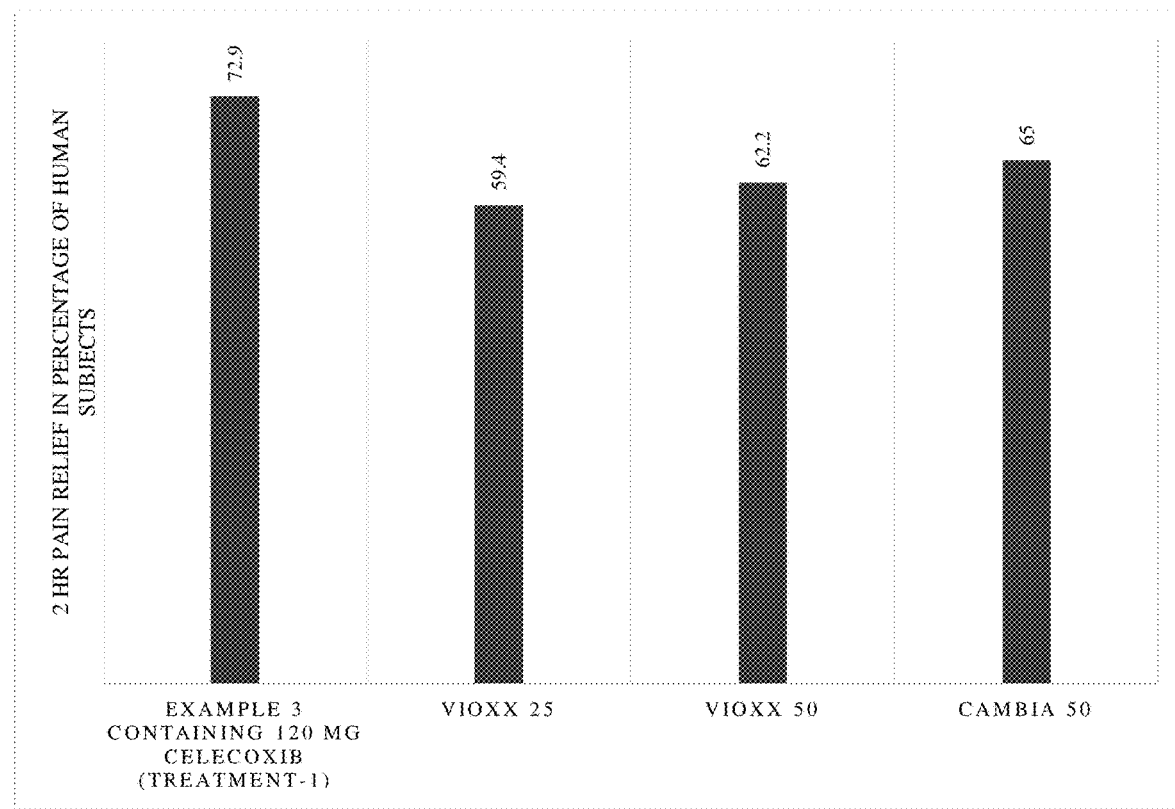
FIG. 5 shows percentage pain relief in percentage of human subjects at 2 hours results of the Example 3 having 120 mg Celecoxib (Treatment-1) compared to VIOXX 25, VIOXX 50 & CAMBIA 50.

Results:

FIG. 4 shows pain free in percentage of human subjects at 2 hours results of the Example 3 having 120 mg Celecoxib (Treatment-1) compared to Vioxx (25 mg, 50 mg) and Cambia (50 mg). FIG. 5 shows pain relief in percentage of human subjects at 2 hours results of the Example 3 having 120 mg Celecoxib (Treatment-1) compared to VIOXX 25 (25 mg), VIOXX 50 (50 mg) and CAMBIA 50 (50 mg).

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

What is claimed is:

1. An oral pharmaceutical composition, comprising at least a 20% reduced dose of celecoxib relative to conventional celecoxib in 400 mg oral capsules and a medium chain glyceride, wherein said composition upon oral administration to a human subject under fasting conditions, provides at least one of the following pharmacokinetic parameters:

a. AUC(0-15 min) of at least about 10 ng·h/mL;
b. AUC(0-30 min) of at least about 80 ng·h/mL;
c. AUC(0-1 hr) of at least about 400 ng·h/mL;
d. AUC(0-2 hr) of at least about 1000 ng·h/mL;
e. AUC(0-t) of at least about 2000 ng·h/mL;
f. AUC(0-∞) of at least about 2000 ng·h/mL; and
g. Tlag of not more than 8 minutes.

2. The composition of claim 1, wherein said composition further comprises at least one pharmaceutically-acceptable excipient.

3. The composition of claim 1, wherein said composition comprises at least about 40% less celecoxib compared to conventional 400 mg oral celecoxib capsules.

4. The composition of claim 1, wherein said composition comprises at least about 55% less celecoxib compared to conventional 400 mg oral celecoxib capsules.

5. The composition of claim 1, wherein said composition comprises at least about 70% less celecoxib compared to conventional 400 mg oral celecoxib capsules.

6. The composition of claim 1, wherein said reduced dose of celecoxib is about 320 mg.

7. The composition of claim 3, wherein said reduced dose of celecoxib is about 240 mg.

8. The composition of claim 4, wherein said reduced dose of celecoxib is about 180 mg.

9. The composition of claim 5, wherein said reduced dose of celecoxib is about 120 mg.

10. The composition of claim 1, wherein said composition is in the form of a solution, suspension, emulsion or liquid mixture.

11. The composition of claim 1, wherein said composition further comprises at least one solubilizer in an amount of from about 10% to about 70% by weight, based on the total weight of the composition.

12. The composition of claim 1, wherein the medium chain glyceride is present in an amount of from about 5% to about 75% by weight, based on the total weight of the composition.

13. The composition of claim 1, wherein said composition further comprises at least one solvent in an amount of from about 20% to about 80% by weight, based on the total weight of the composition.

14. The composition of claim 1, wherein said composition is essentially free of precipitation inhibitors.

15. The composition of claim 1, wherein said composition has a pH of from about 3 to about 7.

16. The composition of claim 1, wherein said composition does not show any precipitation in Fasted-State Simulated Gastric Fluid (FaSSGF) at pH of 2.0, temperature of 37° C.±0.5° C. and under stirring at a speed of 50 rpm, when measured at 60 min.

17. A method of providing a human subject pain relief within 2 hours, comprising administering to the subject an oral composition comprising at least a 20% reduced dose of celecoxib relative to conventional celecoxib in 400 mg oral capsules and a medium chain glyceride, wherein said composition upon oral administration to a human subject under fasting conditions, provides at least one of the following pharmacokinetic parameters:

h. AUC(0-15 min) of at least about 10 ng·h/mL;
i. AUC(0-30 min) of at least about 80 ng·h/mL;
j. AUC(0-1 hr) of at least about 400 ng·h/mL;
k. AUC(0-2 hr) of at least about 1000 ng·h/mL;
l. AUC(0-t) of at least about 2000 ng·h/mL;
m. AUC(0-∞) of at least about 2000 ng·h/mL; and
n. Tlag of not more than 8 minutes.

18. The method claim 17, wherein said reduced dose of celecoxib is sufficient to render the subject pain free within 2 hours of administering the composition.

19. The method of claim 17, wherein said pain is acute pain, migraine pain, cluster headache, neuropathic pain, post-operative pain, chronic lower back pain, herpes neuralgia pain, phantom limb pain, central pain, dental pain, neuropathic pain, opioid-resistant pain, visceral pain, surgical pain, bone injury pain, pain during labor and delivery, pain resulting from burns, sunburn pain, post-partum pain, angina pain, genitourinary tract-related pain, cystitis pain, arthritis pain, inflammation pain, osteoarthritis pain, juvenile rheumatoid arthritis pain, ankylosing spondylitis pain, or primary dysmenorrhea pain.

20. The method of claim 17, wherein said composition comprises at least about 40% less celecoxib compared to conventional 400 mg oral celecoxib capsules.

21. The method of claim 17, wherein said composition comprises at least about 55% less celecoxib compared to conventional 400 mg oral celecoxib capsules.

22. The method of claim 17, wherein said composition comprises at least about 70% less celecoxib compared to conventional 400 mg oral celecoxib capsules.

23. The method of claim 17, wherein said composition further comprises at least one pharmaceutically-acceptable excipient.

24. The method of claim 17, wherein said composition is in the form of a solution, suspension, emulsion, or liquid mixture.

25. The method of claim 17, wherein said composition is essentially free of precipitation inhibitors.

26. The method of claim 17, wherein said composition has a pH of from about 3 to about 7.

* * * * *